United States Patent
Traverso et al.

(10) Patent No.: US 12,383,495 B2
(45) Date of Patent: Aug. 12, 2025

(54) RESIDENT ARTICLES FOR GRAM-LEVEL DOSING

(71) Applicants: Massachusetts Institute of Technology, Cambridge, MA (US); The Brigham and Women's Hospital, Inc., Boston, MA (US)

(72) Inventors: Carlo Giovanni Traverso, Newton, MA (US); Robert S. Langer, Newton, MA (US); Andrew Bellinger, Wellesley, MA (US); Tyler Grant, Arlington, MA (US); Malvika Verma, Cambridge, MA (US); Taylor Bensel, Walpole, MA (US); Daniel Minahan, Weymouth, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 994 days.

(21) Appl. No.: 16/427,560

(22) Filed: May 31, 2019

(65) Prior Publication Data
US 2019/0366064 A1 Dec. 5, 2019

Related U.S. Application Data

(60) Provisional application No. 62/817,477, filed on Mar. 12, 2019, provisional application No. 62/678,471, filed on May 31, 2018, provisional application No. 62/678,492, filed on May 31, 2018, provisional application No. 62/678,439, filed on May 31, 2018.

(51) Int. Cl.
| | | |
|---|---|---|
| *A61K 9/00* | (2006.01) | |
| *A61B 17/50* | (2006.01) | |
| *A61B 17/52* | (2006.01) | |
| *A61K 9/20* | (2006.01) | |
| *A61K 31/133* | (2006.01) | |
| *A61K 31/4409* | (2006.01) | |
| *A61K 31/4709* | (2006.01) | |
| *A61K 31/496* | (2006.01) | |
| *A61K 31/4965* | (2006.01) | |
| *A61K 31/65* | (2006.01) | |
| *A61M 25/00* | (2006.01) | |
| *A61M 25/01* | (2006.01) | |

(Continued)

(52) U.S. Cl.
CPC ............ *A61K 9/0065* (2013.01); *A61B 17/50* (2013.01); *A61B 17/52* (2013.01); *A61K 9/0092* (2013.01); *A61K 9/2027* (2013.01); *A61K 9/2054* (2013.01); *A61K 31/133* (2013.01); *A61K 31/4409* (2013.01); *A61K 31/4709* (2013.01); *A61K 31/496* (2013.01); *A61K 31/4965* (2013.01); *A61K 31/65* (2013.01); *A61M 25/0041* (2013.01); *A61M 25/0127* (2013.01); *A61M 31/00* (2013.01); *A61M 31/002* (2013.01); *A61B 2017/00039* (2013.01); *A61B 2017/00818* (2013.01); *A61B 2017/00862* (2013.01); *A61B 2017/00867* (2013.01); *A61B 2017/00876* (2013.01); *A61K 9/2072* (2013.01); *A61M 2205/0216* (2013.01); *A61M 2205/0266* (2013.01); *A61M 2205/0288* (2013.01); *A61M 2205/3317* (2013.01); *A61M 2205/3327* (2013.01); *A61M 2210/105* (2013.01); *A61M 2210/1053* (2013.01)

(58) Field of Classification Search
CPC ............... A61K 9/0065; A61K 9/0092; A61M 25/0127; A61M 31/002
See application file for complete search history.

(56) References Cited

U.S. PATENT DOCUMENTS

| | | |
|---|---|---|
| 3,847,157 A | 11/1974 | Caillouette |
| 4,758,436 A | 7/1988 | Caldwell et al. |

(Continued)

FOREIGN PATENT DOCUMENTS

| | | |
|---|---|---|
| EP | 0388234 A1 | 9/1990 |
| JP | 2003-093332 A | 4/2003 |

(Continued)

OTHER PUBLICATIONS

Evaluation of a New Antibacterial Agent: Doxycycline Monohydrate and Doxycycline Hyclate (Vibramycin). JAMA. 1969;209(4):549-550 (Year: 1969).*

(Continued)

*Primary Examiner* — Abigail Vanhorn
(74) *Attorney, Agent, or Firm* — Wolf, Greenfield & Sacks, P.C.

(57) ABSTRACT

Drug delivery articles, resident articles, and retrieval systems e.g., for gram-level dosing, are generally provided. In some embodiments, the articles are configured for transesophageal administration, transesophageal retrieval, and/or gastric retention to/in a subject. In certain embodiments, the article includes dimensions configured for transesophageal administration with a gastric resident system. In some cases, the article may be configured to control drug release e.g., with zero-order drug kinetics with no potential for burst release for weeks to months. In some embodiments, the articles described herein comprise biocompatible materials and/or are safe for gastric retention. In certain embodiments, the article includes dimensions configured for transesophageal retrieval. In some cases, the articles described herein may comprise relatively large doses of drug (e.g., greater than or equal to 1 gram).

11 Claims, 31 Drawing Sheets

(51) Int. Cl.
*A61M 31/00* (2006.01)
*A61B 17/00* (2006.01)

(56) References Cited

U.S. PATENT DOCUMENTS

| | | | |
|---|---|---|---|
| 4,925,446 | A | 5/1990 | Garay et al. |
| 5,096,763 | A | 3/1992 | Ogata et al. |
| 5,443,843 | A | 8/1995 | Curatolo et al. |
| 5,663,701 | A | 9/1997 | Kaura |
| 5,902,238 | A | 5/1999 | Golden et al. |
| 6,203,493 | B1 | 3/2001 | Shlomo |
| 6,797,283 | B1 | 9/2004 | Edgren |
| 8,801,694 | B2 | 8/2014 | Lee et al. |
| 9,943,335 | B2 | 4/2018 | Gittard et al. |
| 11,576,860 | B2 | 2/2023 | Traverso et al. |
| 11,850,034 | B2 * | 12/2023 | Langer ............... A61B 5/6871 |
| 2003/0208103 | A1 | 11/2003 | Sonnenschein et al. |
| 2006/0020278 | A1 | 1/2006 | Burnett et al. |
| 2007/0156248 | A1 * | 7/2007 | Marco ................ A61F 5/003 623/23.65 |
| 2009/0105531 | A1 | 4/2009 | Boyden |
| 2009/0112248 | A1 | 4/2009 | Maloney |
| 2009/0149833 | A1 * | 6/2009 | Cima ................ A61K 31/167 604/93.01 |
| 2010/0094116 | A1 | 4/2010 | Silverstein |
| 2010/0152590 | A1 * | 6/2010 | Moore ................ A61B 8/4461 600/466 |
| 2011/0218488 | A1 * | 9/2011 | Boyko ............. A61M 31/002 604/57 |
| 2013/0017264 | A1 | 1/2013 | Khandare et al. |
| 2014/0163664 | A1 | 6/2014 | Goldsmith |
| 2017/0027608 | A1 | 2/2017 | Papadimitrakopoulos et al. |
| 2017/0049598 | A1 | 2/2017 | Kalloo et al. |
| 2017/0106099 | A1 * | 4/2017 | Bellinger ........... A61K 47/6901 |
| 2017/0157360 | A1 | 6/2017 | Cima et al. |
| 2017/0218537 | A1 | 8/2017 | Olivares |
| 2017/0266112 | A1 | 9/2017 | Bellinger et al. |
| 2019/0307592 | A1 | 10/2019 | Hibri |
| 2019/0365418 | A1 | 12/2019 | Traverso et al. |
| 2019/0365645 | A1 * | 12/2019 | Traverso ............ A61K 31/4409 |
| 2021/0353174 | A1 * | 11/2021 | Langer ............... A61M 31/00 |
| 2024/0108241 | A1 * | 4/2024 | Langer ............... A61B 5/6871 |

FOREIGN PATENT DOCUMENTS

| | | |
|---|---|---|
| WO | WO 99/48481 A1 | 9/1999 |
| WO | WO 2008/057887 A2 | 5/2008 |
| WO | WO 2011/096827 A1 | 8/2011 |
| WO | WO-2015200752 A1 * | 12/2015 ........... A61K 9/0034 |

OTHER PUBLICATIONS

Merriam-Webster, discrete, obtained online at https://www.merriam-webster.com/dictionary/discrete, downloaded on Oct. 11, 2024. (Year: 2024).*

Britannica.com, Esophagus, obtained online at: https://www.britannica.com/science/human-digestive-system/Esophagus, downloaded on Oct. 11, 2024. (Year: 2024).*

Altreuter, David H., et al. "Changing the pill: developments toward the promise of an ultra-long-acting gastroretentive dosage form." Expert opinion on drug delivery 15.12 (2018): 1189-1198. (Year: 2018).*

International Search Report and Written Opinion mailed Sep. 9, 2019 for Application No. PCT/US2019/034790.

International Search Report and Written Opinion mailed Sep. 9, 2019 for Application No. PCT/US2019/034792.

International Search Report and Written Opinion mailed Sep. 9, 2019 for Application No. PCT/US2019/034796.

[No Author Listed] Empty Capsule Size Chart. Available at: https://www.capsuline.com/empty-capsule-size-chart/. (Accessed: Feb. 19, 2018).

[No Author Listed] Global Tuberculosis Report 2017. WHO. 2017. doi:WHO/HTM/TB/2017.23.

[No Author Listed] Guidelines for treatment of tuberculosis. 4th Ed. WHO. 2010. 160 pages.

Aguirre et al., An endoluminal sleeve induces substantial weight loss and normalizes glucose homeostasis in rats with diet-induced obesity. Obesity (Silver Spring). Dec. 2008;16(12):2585-92. doi:10.1038/oby.2008.502. Epub Oct. 30, 2008.

Akhgari et al., Prediction of Optimum Combination of Eudragit RS/Eudragit RL/Ethyl Cellulose Polymeric Free Films Based on Experimental Design for Using as a Coating System for Sustained Release Theophylline Pellets. Adv Pharm Bull. Jun. 2016;6(2):219-25. doi: 10.15171/apb.2016.030. Epub Jun. 30, 2016.

Arinaminpathy et al., Understanding the incremental value of novel diagnostic tests for tuberculosis. Nature. Dec. 3, 2015;528(7580):S60-7. doi: 10.1038/nature16045.

Behary et al., Advances in the Endoscopic Management of Obesity. Gastroenterol Res Pract. 2015;2015:757821. Epub May 28, 2015. doi: 10.1155/2015/757821.

Bellinger et al., Oral, ultra-long-lasting drug delivery: Application toward malaria elimination goals. Sci Transl Med. Nov. 16, 2016;8(365):365ra157. 25 pages. Author Manuscript.

Bliziotis et al., Effect of aminoglycoside and beta-lactam combination therapy versus beta-lactam monotherapy on the emergence of antimicrobial resistance: a meta-analysis of randomized, controlled trials. Clin Infect Dis. Jul. 15, 2005;41(2):149-58. Epub May 31, 2005.

Blomberg et al., The rationale for recommending fixed-dose combination tablets for treatment of tuberculosis. Bull World Health Organ. 2001;79(1):61-8. Epub Nov. 5, 2003.

Burkersroda et al., Why degradable polymers undergo surface erosion or bulk erosion. Biomaterials. Nov. 2002;23(21):4221-31.

Bussemer et al., Pulsatile drug-delivery systems. Crit Rev Ther Drug Carrier Syst. 2001;18(5):433-58.

Campbell et al., Structural mechanism for rifampicin inhibition of bacterial rna polymerase. Cell. Mar. 23, 2001;104(6):901-12.

Chambers et al., Waves of resistance: *Staphylococcus aureus* in the antibiotic era. Nat Rev Microbiol. Sep. 2009;7(9):629-41. doi: 10.1038/nrmicro2200. Author Manuscript. 31 pages.

Choudhry et al., Full Coverage for Preventive Medications after Myocardial Infarction. N Engl J Med 2011;365:2088-97. doi: 10.1056/NEJMsa1107913. Epub: Nov. 14, 2011.

Coash et al., Endoscopic removal of a long sharp metallic foreign body by a snared magnet: an attractive solution. J Dig Dis. Apr. 2012;13(4):239-41. doi: 10.1111/j.1751-2980.2012.00573.x.

Cullen et al., Nebulized lidocaine decreases the discomfort of nasogastric tube insertion: a randomized, double-blind trial. Ann Emerg Med. Aug. 2004;44(2):131-7.

Dantas et al., Context matters—the complex interplay between resistome genotypes and resistance phenotypes. Curr Opin Microbiol. Oct. 2012;15(5):577-82. doi: 10.1016/j.mib.2012.07.004. Epub Sep. 3, 2012.

Dantas et al., How to Fight Back Against Antibiotic Resistance. Am. Scientist. Jan.-Feb. 2014;102:42-51.

Davies et al., Release characteristics, ovarian activity and menstrual bleeding pattern with a single contraceptive implant releast 3-ketodesogestrel. Contraception. 1993;47:251-261.

Diehl et al., Endoscopic retrieval devices. Gastrointest Endosc. May 2009;69(6):997-1003. doi: 10.1016/j.gie.2009.01.005.

Du Toit et al., Tuberculosis chemotherapy: current drug delivery approaches. Respir Res. Sep. 19, 2006;7:118.

Dutta et al., Can the duration of tuberculosis treatment be shortened with higher dosages of rifampicin? Front Microbiol. 2015; 6: 1117. Epub Oct. 14, 2015. doi: 10.3389/fmicb.2015.01117.

El Feninat et al., Shape Memory Materials for Biomedical Applications. Adv. Eng. Mater. Mar. 13, 2002;4(3):91-104. https://doi.org/10.1002/1527-2648(200203)4:3<91 ::AID-ADEM91>3.0.CO;2-B.

Equen et al., Magnetic removal of foreign bodies from the esophagus, stomach and duodenum. AMA Arch Otolaryngol. Dec. 1957;66(6):698-706.

(56) References Cited

OTHER PUBLICATIONS

Erhabor et al., Directly Observed Short Course Therapy for Tuberculosis—A Preliminary Report of a Three-Year Experience in a Teaching Hospital. J. Natl. Med. Assoc. 2003;95:1082-1088.

Farra et al., First-in-human testing of a wirelessly controlled drug delivery microchip. Sci Transl Med. Feb. 22, 2012;4(122):122ra21, 12 pages. doi: 10.1126/scitranslmed.3003276. Epub Feb. 16, 2012.

Ferrua et al., Modeling the Fluid Dynamics in a Human Stomach to Gain Insight of Food Digestion. J Food Sci. Sep. 2010; 75(7): R151-R162. doi: 10.1111/j.1750-3841.2010.01748.x.

Freire et al., Gastric-resistant isoniazid pellets reduced degradation of rifampicin in acidic medium. Brazilian J. Pharm. Sci. Oct./Dec. 2014;50(4):749-55. http://dx.doi.org/10.1590/S1984-82502014000400010.

Fuentes-Hernandez et al., Using a Sequential Regimen to Eliminate Bacteria at Sublethal Antibiotic Dosages. PLoS Biol. Apr. 2015; 13(4): e1002104. EPub Apr. 8, 2015. doi: 10.1371/journal.pbio.1002104. 17 pages.

Gao et al., Poly(dimethylsiloxane) coatings for controlled drug release. III. Drug release profiles and swelling properties of the free-standing films. J Appl Polym Sci. Apr. 15, 2005;96(2):494-501. doi: https://doi.org/10.1002/app.21469.

Gimeno et al., A controlled antibiotic release system to prevent orthopedic-implant associated infections: An in vitro study. Eur J Pharm Biopharm. Oct. 2015; 96: 264-271. doi: 10.1016/j.ejpb.2015.08.007.

Gninafon et al., Outcome of tuberculosis retreatment in routine condition in Cotonou, Benin. Int. J. Tuberc. Lung. Dis. 2004;8(10):1241-7.

Gupta et al., Animal models of tuberculosis. Tuberculosis (Edinb). Sep.-Nov. 2005;85(5-6):277-93. Epub Oct. 24, 2005.

Gurpinar et al., Removal of ingested metallic foreign bodies from children by orogastric magnetic tube. Minimally Invasiv Ther Allied Tech. 1997;6:469-471. Epub Jul. 10, 2009. https://doi.org/10.3109/13645709709153354.

Hager et al., Shape memory polymers: Past, present and future developments. Prog Polym Sci. 2015;49-50:3-33. doi: 10.1016/j.progpolymsci.2015.04.002.

Hancock et al., The Relative Densities of Pharmaceutical Powders, Blends, Dry Granulations, and Immediate-Release Tablets. Pharm Technol. 2003;27:64-80.

Hanna et al., Improving the safety of nasogastric feeding tube insertion: Developing guidline for the safe verification of feeding tub position—a decision analysis approach. NHS Patient Safety Research Portfolio Report. Jul. 2010; 1:1-99.

Hartmann et al., The specific inhibition of the DNA-directed RNA synthesis by rifamycin. Biochim Biophys Acta. 1967;145(3):843-4.

Huang et al., Degradation characteristics of poly(ε-caprolactone)-based copolymers and blends. J. Appl. Polym. Sci. Oct. 15, 2006;102(2):1681-7. https://doi.org/10.1002/app.24196. Epub Jul. 28, 2006.

Imamovic et al., Use of collateral sensitivity networks to design drug cycling protocols that avoid resistance development. Sci Transl Med. Sep. 25, 2013;5(204):204ra132. doi: 10.1126/scitranslmed.3006609.

Inkenberry et al., Management of ingested foreign bodies and food impactions. Gastrointest Endosc. Jun. 2011;73(6):1085-91. doi: 10.1016/j.gie.2010.11.010.

Jaiswar et al., Hot Melt Extrusion: Continuous Process of Preparation of Sustained Released Matrix Tablet by Using Hydroxypropylcellulose . American Journal of PharmTech Research. 2015;6(1):295-312.

Karumbi et al., Directly observed therapy for treating tuberculosis. Cochrane Database Syst Rev. May 29, 2015;(5):CD003343. doi: 10.1002/14651858.CD003343.pub4.

Kim et al., Alternating antibiotic treatments constrain evolutionary paths to multidrug resistance. Proc Natl Acad Sci U S A. Oct. 7, 2014;111(40):14494-9. doi: 10.1073/pnas.1409800111. Epub Sep. 22, 2014.

Kirtane et al., Development of an oral once-weekly drug delivery system for HIV antiretroviral therapy. Nat Commun. Jan. 9, 2018;9(1):2. doi: 10.1038/s41467-017-02294-6.

Kulkarni et al., Non-adherence of new pulmonary tuberculosis patients to anti-tuberculosis treatment. Ann Med Health Sci Res. Jan. 2013;3(1):67-74. doi: 10.4103/2141-9248.109507.

Kumar et al., Polyanhydrides: an overview. Adv Drug Deliv Rev. Oct. 16, 2002;54(7):889-910.

Lázár et al., Bacterial evolution of antibiotic hypersensitivity. Mol Syst Biol. Oct. 29, 2013;9:700. doi: 10.1038/msb.2013.57.

Lee et al., A Janus Mucoadhesive and Omniphobic Device for Gastrointestinal Retention. Adv Healthc Mater. May 2016;5(10):1141-6. doi: 10.1002/adhm.201501036. Epub Apr. 6, 2016.

Lee et al., An intravesical device for the sustained delivery of lidocaine to the bladder. J Contr Rel. Jan. 20, 2011;149(2):133-9. doi: 10.1016/j.jconrel.2010.10.016. Epub Oct. 30, 2010.

Lendlein et al., Shape-memory polymers. Angew Chem Int Ed Engl. Jun. 17, 2002;41(12):2035-57.

Lewandowski et al., Global Tuberculosis Report. WHO 2015;1:1689-1699.

Lewis et al., Clinical indicators of mycobacteraemia in adults admitted to hospital in Blantyre. Malawi Med Journal. Jun. 2003; 15(2):56-60.

Lewis, Platforms for antibiotic discovery. Nat Rev Drug Discov. May 2013;12(5):371-87. doi: 10.1038/nrd3975.

Luborsky et al., Recent Advances in the Removal of Magnetic Foreign Bodies from the Esophagus, Stomach and Duodenum with Controllable Permanent Magnets. Am J Roentgenol Radium Ther Nucl Med. Nov. 1964;92:1021-5.

Mandeville et al., Gastroenterology in developing countries: issues and advances. World J Gastroenterol. Jun. 21, 2009;15(23):2839-54.

Mariappan et al., Regional gastrointestinal permeability of rifampicin and isoniazid (alone and their combination) in the rat. Int J Tuberc Lung Dis. Aug. 2003;7(8):797-803.

Maroni et al., Oral pulsatile drug delivery systems. Expert Opin Drug Deliv. Sep. 2005;2(5):855-71.

Meurens et al., The pig: a model for human infectious diseases. Trends Microbiol. Jan. 2012;20(1):50-7. doi: 10.1016/j.tim.2011.11.002. Epub Dec. 5, 2011.

Mintchev et al., Pilot study of temporary controllable gastric pseudobezoars for dynamic non-invasive gastric volume reduction. Physiol. Meas. 2010;31:131-144. doi:10.1088/0967-3334/31/2/001.

Mintz et al., Hybrid natural orifice translumenal surgery (Notes) sleeve gastrectomy: a feasibility study using an animal model. Surg Endosc. Aug. 2008;22(8):1798-802. doi: 10.1007/s00464-008-9915-y. Epub Apr. 25, 2008.

Mitchison et al., The chemotherapy of tuberculosis: past, present and future. Int J Tuberc Lung Dis. Jun. 2012;16(6):724-32. doi: 10.5588/ijtld.12.0083.

Muggli et al., Crosslinked polyanhydrides for use in orthopedic applications: degradation behavior and mechanics. J Biomed Mater Res. Aug. 1999;46(2):271-8.

Nayak et al., Gastroretentive drug delivery systems: A review. Asian J. Pharm. Clin. Res. Jan.-Mar. 2010;3(1):2-10.

Nelson et al., ASGE technology status evaluation report. Endoscopic retrieval devices. Feb. 1999. American Society for Gastrointestinal Endoscopy. Gastrointest Endosc. Dec. 1999;50(6):932-4.

Ouimet et al., Biodegradable Ferulic Acid-containing Poly(anhydride-ester): Degradation Products with Controlled Release and Sustained Antioxidant Activity. Biomacromolecules. Mar. 11, 2013; 14(3):854-861. EPub Feb. 4, 2013. doi: 10.1021/bm3018998.

Pál et al., Collateral sensitivity of antibiotic-resistant microbes. Trends Microbiol. Jul. 2015;23(7):401-7. doi: 10.1016/j.tim.2015.02.009. Epub Mar. 25, 2015.

Patel et al., Pulsatile Drug Delivery System : a Review. IJPSR. Sep. 1, 2015;6(9):3676-88.

Paul et al., Beta lactam antibiotic monotherapy versus beta lactam-aminoglycoside antibiotic combination therapy for sepsis. Cochrane Database Syst Rev. Jan. 7, 2014;(1):CD003344. doi: 10.1002/14651858.CD003344.pub3.

Pham et al., Pulmonary drug delivery systems for tuberculosis treatment. Int J Pharm. Jan. 30, 2015;478(2):517-29. doi:10.1016/j.ijpharm.2014.12.009. Epub Dec. 10, 2014.

(56) References Cited

OTHER PUBLICATIONS

Phillips et al., Gastric trichobezoar: case report and literature review. Mayo Clin Proc. Jul. 1998;73(7):653-6.
Prajapati et a., Raft forming system-an upcoming approach of gastroretentive drug delivery system. J Control Release. Jun. 10, 2013;168(2):151-65. doi: 10.1016/j.jconrel.2013.02.028. Epub Mar. 14, 2013.
Reddy et al., Review on: Pulsatile Druge Delivery Systems. J. Pharm. Sci. & Res. Jan. 2009;1(4):109-115.
Riva, From milk to rifampicin and back again: history of failures and successes in the treatment for tuberculosis. J Antibiot (Tokyo). Sep. 2014;67(9):661-5. doi: 10.1038/ja.2014.108. Epub Aug. 6, 2014.
Rodriguez De Evgrafov et al., Collateral Resistance and Sensitivity Modulate Evolution of High-Level Resistance to Drug Combination Treatment in *Staphylococcus aureus*. Mol Biol Evol. May 2015;32(5):1175-85. doi: 10.1093/molbev/msv006. Epub Jan. 23, 2015.
Roth et al., Assessment of juvenile pigs to serve as human pediatric surrogates for preclinical formulation pharmacokinetic testing. AAPS J. Jul. 2013;15(3):763-74. doi: 10.1208/s12248-013-9482-6. Epub Apr. 18, 2013.
Rutta et a., Treatment outcome among Rwandan and Burundian refugees with sputum smear-positive tuberculosis in Ngara, Tanzania. Int J Tuberc Lung Dis. Jul. 2001;5(7):628-32.
Sabate, Adherence to long-term therapy: Evidence for Action. 2003. 209 pages.
Salessiotis, Measurement of the diameter of the pylorus in man: Part I. Experimental project for clinical application. Am. J. Surgery. Sep. 1972;124(3):331-333. doi: 10.1016/0002-9610(72)90036-0. Epub Mar. 18, 2004.
Schulze., Imaging and modelling of digestion in the stomach and the duodenum. Neurogastroenterol Motil. Mar. 2006;18(3):172-83.
Shanbhag et al., Application of cellulose acetate butyrate-based membrane for osmotic drug delivery. Cellulose. 2007; 14:65-71. doi: 10.1007/s10570-006-9091-y.
Sharma et al., Development of extended release matrices of rifampicin using hot melt extursion technique. J. Appl. Pharm. Sci. Oct. 2013;3(10):30-8. doi: 10.7324/JAPS.2013.31006.
Smith et al., Animal models for experimental tuberculosis. Clin Infect Dis. Sep. 2000;31 Suppl 3:S68-70.
Stebbins et al., Antibiotic-containing polymers for localized, sustained drug delivery. Adv Drug Deliv Rev. Nov. 30, 2014;78:77-87. doi: 10.1016/j.addr.2014.04.006. Epub Apr. 18, 2014. Author Manuscript. 25 pages.
Steingart et al., Higher-dose rifampin for the treatment of pulmonary tuberculosis: a systematic review. Int J Tuberc Lung Dis. Mar. 2011; 15(3):305-16.
Streubel et al., Gastroretentive drug delivery systems. Expert Opin Drug Deliv. Mar. 2006;3(2):217-33.
Tiemersma et al., Natural history of tuberculosis: duration and fatality of untreated pulmonary tuberculosis in HIV negative patients: a systematic review. PLoS One. Apr. 4, 2011;6(4):e17601. doi: 10.1371/journal.pone.0017601.
Timmers et al., Pharmacokinetics of etonogestrel and ethinylestradiol released from a combined contraceptive vaginal ring. Clin Pharm. Sep. 2000;39(3):233-42.
Turos et al., Penicillin-Bound Polyacrylate Nanoparticles: Restoring the Activity of β-Lactam Antibiotics Against MRSA. Bioorg Med Chem Lett. Jun. 15, 2007; 17(12): 3468-3472. EPub Mar. 27, 2007. doi: 10.1016/j.bmcl.2007.03.077. Author Manuscript. 14 pages.
Van Ingen et al., Why Do We Use 600 mg of Rifampicin in Tuberculosis Treatment? Clin Infect Dis. May 2011;52(9):e194-9. doi: 10.1093/cid/cir184.
Vasoo et al., Emerging issues in gram-negative bacterial resistance: an update for the practicing clinician. Mayo Clin Proc. Mar. 2015;90(3):395-403. doi: 10.1016/j.mayocp.2014.12.002.
Verma et al., A gastric resident drug delivery system for prolonged gram-level dosing of tuberculosis treatment. Sci Transl Med. Mar. 13, 2019;11(483). pii: eaau6267. doi: 10.1126/scitranslmed. aau6267.
Verma et al., Supplementary Materials for: A gastric resident drug delivery system for prolonged gram-level dosing of tuberculosis treatment. Sci Transl Med. Mar. 13, 2019;11(483). pii: eaau6267. doi: 10.1126/scitranslmed.aau6267.
Young, Animal models of tuberculosis. Eur J Immunol. Aug. 2009;39(8):2011-4. doi: 10.1002/eji.200939542.
Zhang et al., A pH-responsive supramolecular polymer gel as an enteric elastomer for use in gastric devices. Nat Mater. Oct. 2015;14(10):1065-71. doi: 10.1038/nmat4355. Epub Jul. 27, 2015.
Zhang et al., Mechanisms of drug resistance in Mycobacterium tuberculosis. Int J Tuberc Lung Dis. Nov. 2009;13(11):1320-30.
PCT/US2019/034790, Sep. 9, 2019, International Search Report and Written Opinion.
PCT/US2019/034792, Sep. 9, 2019, International Search Report and Written Opinion.
PCT/US2019/034796, Sep. 9, 2019, International Search Report and Written Opinion.
U.S. Appl. No. 16/427,505, filed May 31, 2019, Traverso et al.
U.S. Appl. No. 16/427,414, filed May 31, 2019, Traverso et al.
International Preliminary Report on Patentability for International App. No. PCT/US2019/034790, mailed Dec. 10, 2020.
International Preliminary Report on Patentability for International App. No. PCT/US2019/034792, mailed Dec. 10, 2020.
International Preliminary Report on Patentability for International App. No. PCT/US2019/034796, mailed Dec. 10, 2020.
Amin et al., Lyophilization of polyethylene glycol mixtures. J Pharm Sci. Sep. 2004;93(9):2244-9.
Myllymäki et al., Animal models in tuberculosis research—where is the beef? Expert Opin Drug Discov. 2015;10(8):871-83. doi: 10.1517/17460441.2015.1049529. Epub Jun. 13, 2015. Review.
Vangara et al., Investigation of the Impact of Cellulose Acetate Coating on the Release pattern of Freely Soluble Drug: Metoprolol Succinate. Int. Res. J. Phamr. 2015;6(4):249-255. doi: https://doi.org/10.1007/s10570-006-9091-y.

* cited by examiner

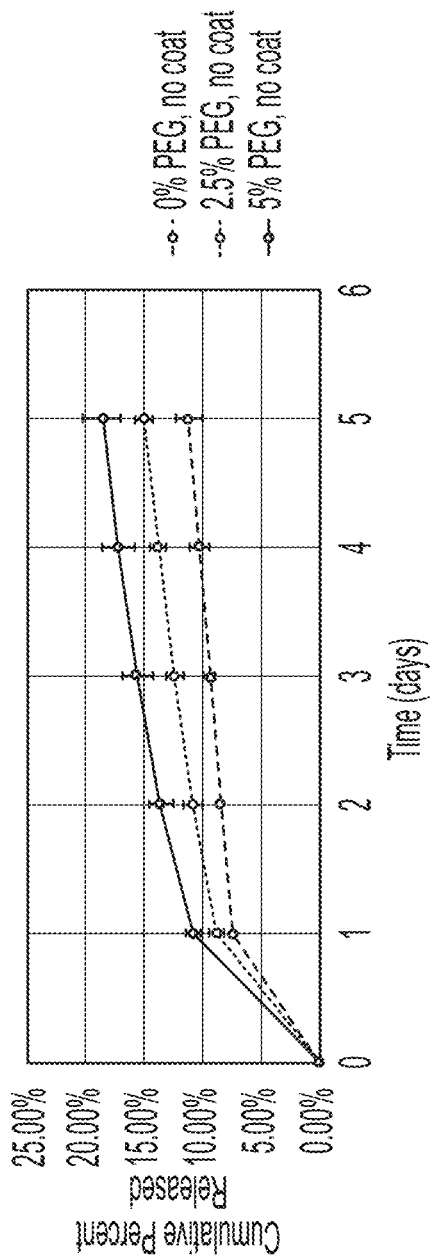
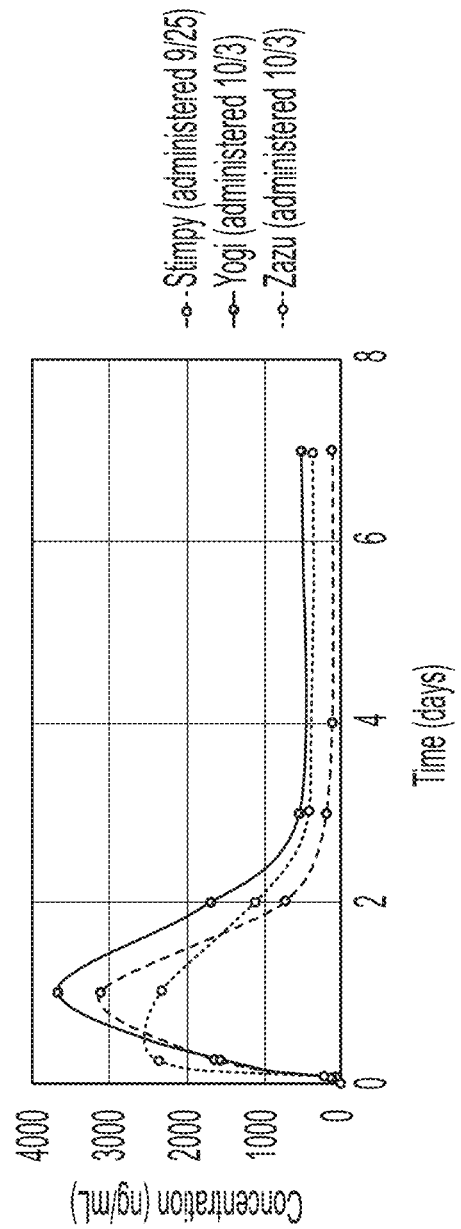
FIG. 3A
FIG. 3B

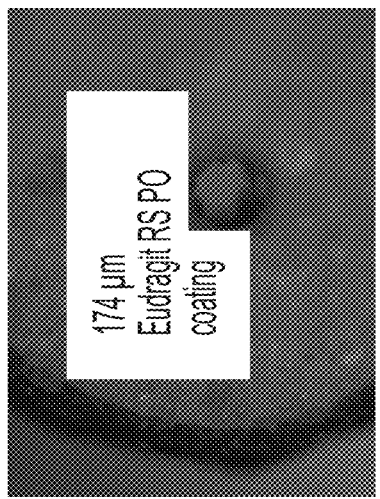
FIG. 4A
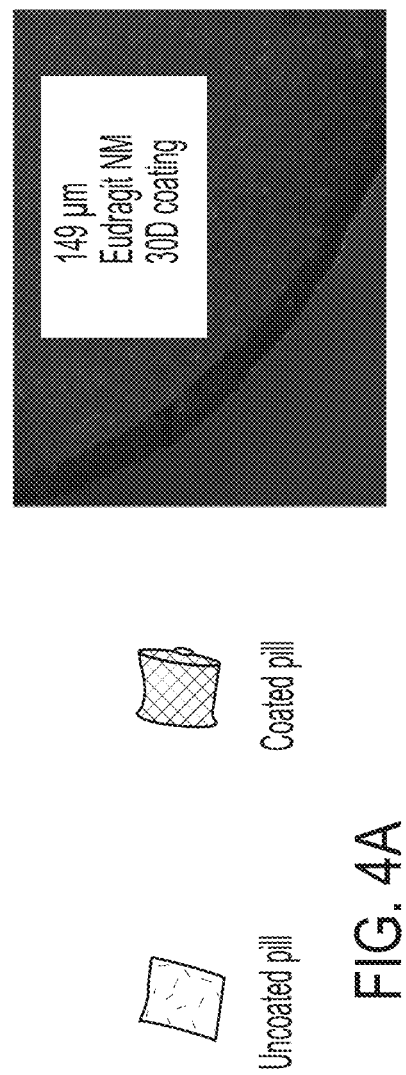
FIG. 4B
FIG. 4C
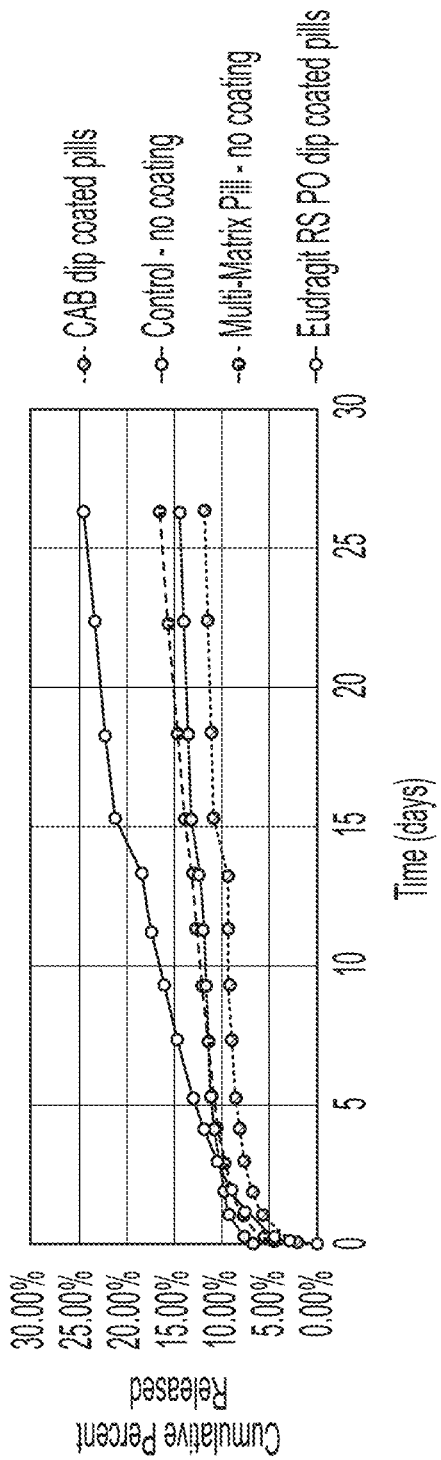
FIG. 4D

Gastric resident system before deployment in vivo
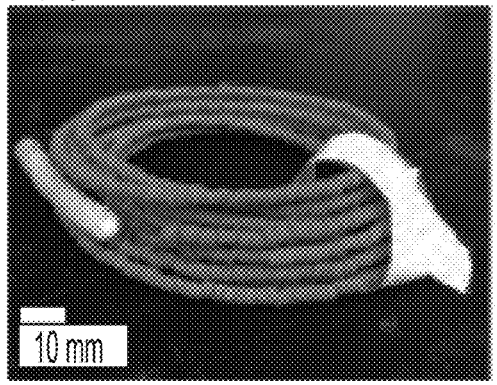
FIG. 10A
Gastric resident system retrieved after 28 days in vivo
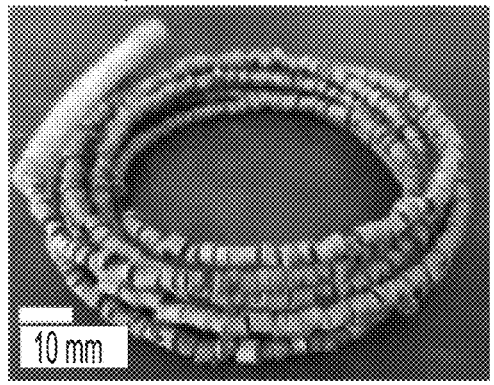
FIG. 10B
Single dose of doxycyline hyclate in vivo
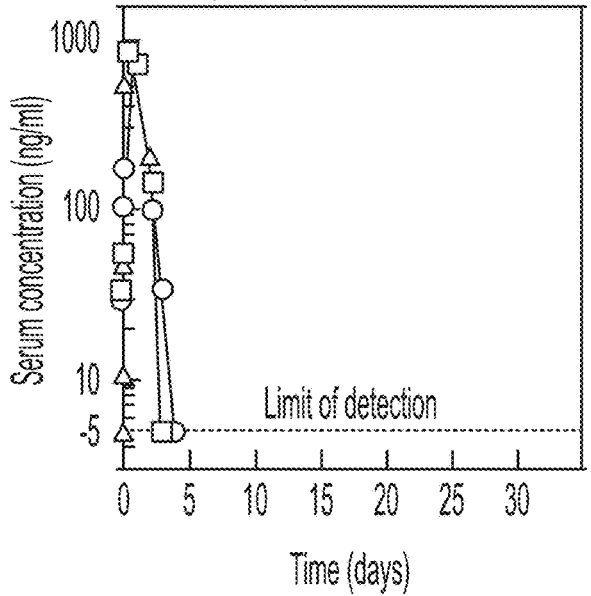
Gastric resident system with doxycyline hyclate in vivo
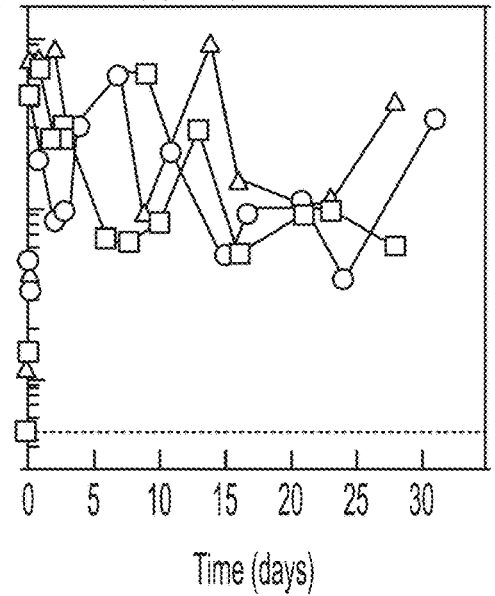
FIG. 10C
| Formulation | Total drug incorporated (g) | AUC (ng/ml x day) | Duration of release (days) |
|---|---|---|---|
| Single dose | 0.1 | 1019 ± 203 | 3 |
| GRS | 10 | 7118 ± 3170 | >28 |
FIG. 10D

| Formulation: Amount | Doxycyline hyclate | Silicone | PEG | Coating: Thickness |
|---|---|---|---|---|
| 1: 1 gram | 32% | 66% | 2% | Eudragit RS 100: 210 μm |
| 2: 2 grams | 32% | 68% | 0% | Eudragit RS 100: 300 μm |
| 3: 3 grams | 32% | 68% | 0% | PCL: 350 μm |
| 4: 4 grams | 32% | 68% | 0% | PCL: 650 μm |

| Option | Description of adherence solution |
|---|---|
| A | Reduce frequency of administering medication |
| B | Send reminders to patients via cell phone or SMS |
| C | Send healthcare worker or family member to remind patient |
| D | Reward patients who take medication |
FIG. 17A
| Option | Route of administration |
|---|---|
| A | Nasogastric tube |
| B | Swallowing 30 "000" capsules |
| C | Drinking 2 Liters of water-drug mixture |
FIG. 17D
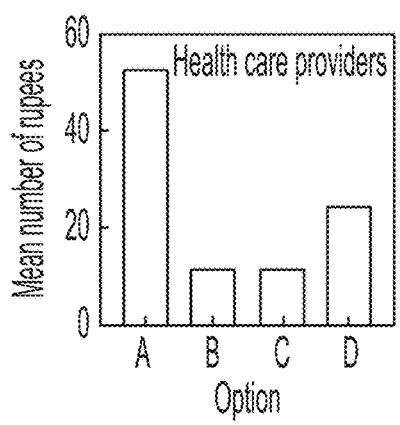
FIG. 17B
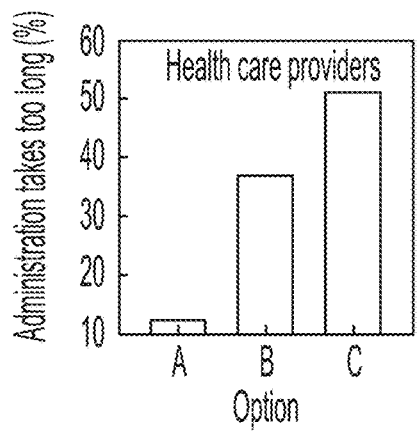
FIG. 17E
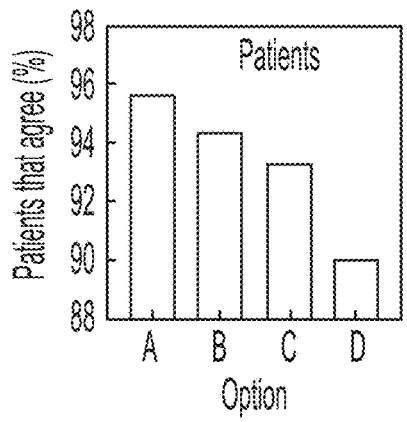
FIG. 17C
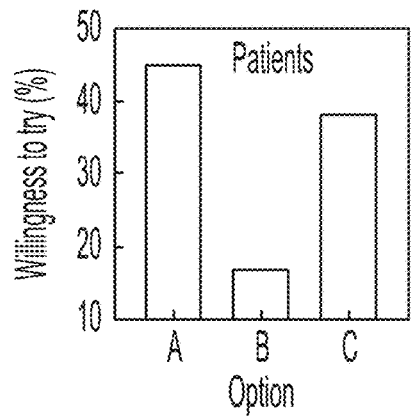
FIG. 17F

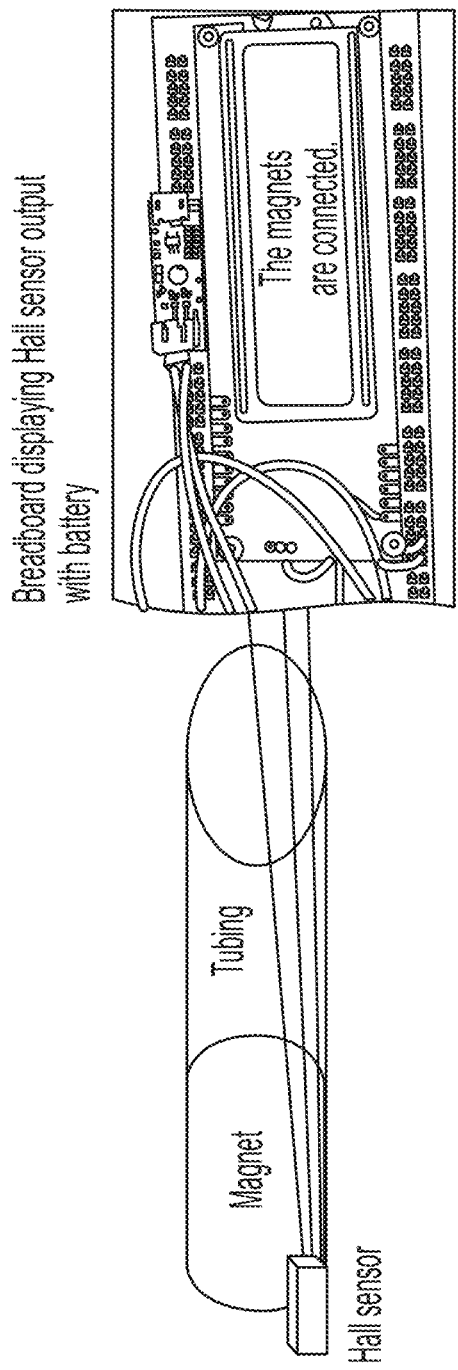
FIG. 24A
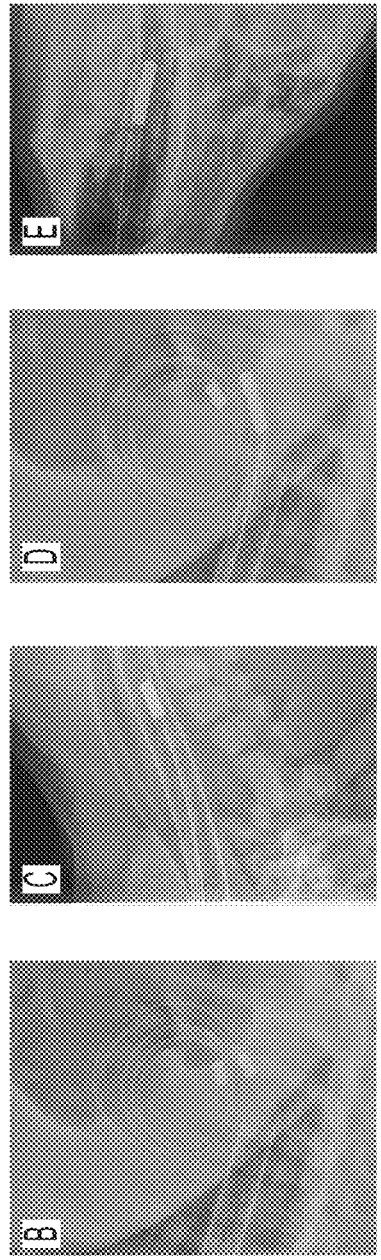
FIG. 24B
FIG. 24C
FIG. 24D
FIG. 24E

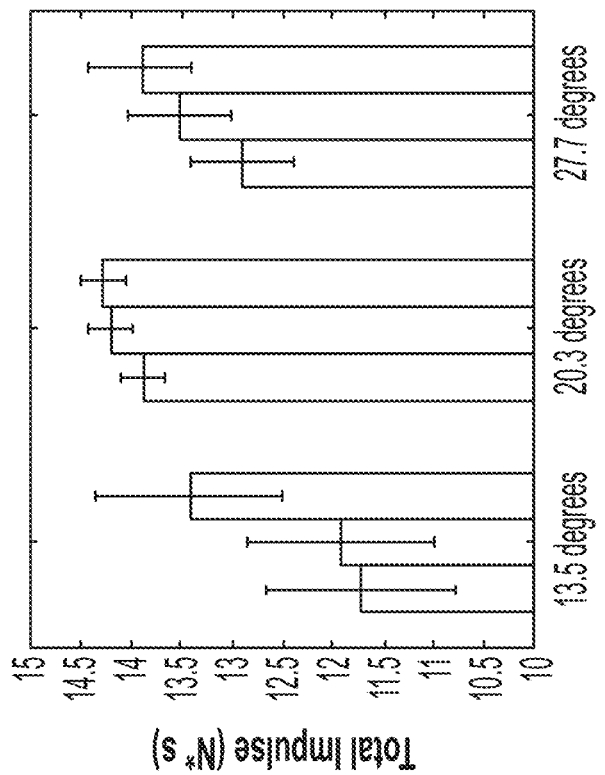
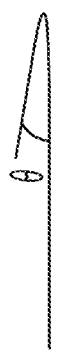
FIG. 26B
FIG. 26A

RESIDENT ARTICLES FOR GRAM-LEVEL DOSING

RELATED APPLICATIONS

This application claims priority under 35 U.S.C. § 119(e) to U.S. Provisional Patent Application Ser. No. 62/678,492, filed May 31, 2018, entitled "DRUG DELIVERY ARTICLES FOR GRAM-LEVEL DOSING," to U.S. Provisional Patent Application Ser. No. 62/817,477, filed Mar. 12, 2019, entitled "DRUG DELIVERY ARTICLES FOR GRAM-LEVEL DOSING," to U.S. Provisional Patent Application Ser. No. 62/678,471, filed May 31, 2018, entitled "RESIDENT ARTICLES FOR GRAM-LEVEL DOSING," and to U.S. Provisional Patent Application Ser. No. 62/678,439, filed May 31, 2018, entitled "RETRIEVAL SYSTEMS AND RELATED METHODS," each of which is incorporated herein by reference in its entirety for all purposes.

STATEMENT OF GOVERNMENT SUPPORT

This invention was made with Government support under Grant No. R37-EB000244 awarded by the National Institutes of Health (NIH). The Government has certain rights in the invention.

FIELD

The present invention generally relates to drug delivery components and resident articles for gram-level dosing. In some embodiments, retrieval systems are provided.

BACKGROUND

Drug adherence to indefinite duration oral therapy is often poor. Recent advances in developing gastric resident systems for long-term drug delivery of medication are addressing the challenge of medication adherence with swallowable systems. However, challenges for these drug delivery devices include, for example, achieving high levels of drug loading, controlling the release rate of drug for an extended period, and preventing the burst release of drug. Additionally, adherence rates to oral therapies for chronic asymptomatic conditions are estimated to be less than 50%. Current pharmacologic solutions to the adherence problem are limited to invasive devices and a restricted subset of pharmacologic agents. Furthermore, extended release orally administered drug delivery systems are limited by the quantity of drug that can fit inside the largest ingestible capsule and therefore cannot be used to treat many diseases with long and frequent dosing regimens.

Accordingly, improved systems, articles and methods are needed.

SUMMARY

The present invention generally relates to drug delivery components and resident articles for gram-level dosing. In some embodiments, retrieval systems are provided.

In one aspect, articles configured for transesophageal administration, transesophageal retrieval, and/or gastric retention are provided. In some embodiments, the article comprises a polymer matrix comprising a polymeric material and a therapeutic agent associated with the polymer matrix and a hollow core disposed within the polymeric matrix and configured to receive an elastic wire.

In some embodiments, the article comprises a polymeric material having a reconfigurable shape and a hollow core and a therapeutic agent associated with the polymeric material, wherein the article has a maximum dimension of greater than or equal to 28 cm and wherein the therapeutic agent is present in the article in an amount greater than or equal to 3 grams.

In another aspect, systems configured for transesophageal retrieval are provided. In some embodiments, the system comprises a polymeric component having a flexible member, a binding component associated with an end portion of the polymeric component, and a sensor associated with an end portion of the polymeric component, wherein the system is configured to pass through a nasogastric and/or endoscopic tube.

In another aspect, methods for retrieving a gastric residence system located internal to a subject are provided. In some embodiments, the method comprises administering transesophageally to a subject a system, the system comprising a polymeric component having a flexible member and a binding component associated with an end portion of the polymeric component, determining, via a sensor associated with an end portion of the polymeric component, a distance between the binding component and the gastric residence system, interfacing, via a locking mechanism associated with an end portion of the polymeric component, the gastric residence system, and removing, transesophageally, the gastric residence system from the location internal to the subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 3A is a plot of cumulative percent drug released versus time (days), according to one set of embodiments;

FIG. 3B is a plot of concentration in ng/mL versus time (days), according to one set of embodiments;

FIG. 4A is a photograph of an uncoated versus coated article, according to one set of embodiments;

FIG. 4B is a photograph of an exemplary coated article, according to one set of embodiments;

FIG. 4C is a photograph of an exemplary coated article, according to one set of embodiments;

FIG. 4D is a plot of cumulative percent drug released versus time (days), according to one set of embodiments;

(FIG. 8A) (i-ii) An NG tube is first placed as a conduit for the large-dose GRS to be non-surgically administered, and then the NG tube is removed from the patient. (iii-iv) The GRS resides in the gastric cavity while releasing drugs. (v-vi) An NG tube is again placed in the patient for deployment of a retrieval device to attach and remove the GRS from the gastric cavity. Black arrows indicate direction of movement of the NG tube and retrieval device, and red arrows indicate drug release. (FIG. 8B) The GRS consists of a series of drug pills on a coiled superelastic nitinol wire; the ends are protected with a retainer and tubing. (FIG. 8C) Representative radiographs of the GRS immediately after deployment and on day 28 in a swine model. Dashed circles indicate GRS location. (FIG. 8D) The retrieval device consists of a Hall effect sensor and a magnet that can detect and attach to the magnets on either end of the GRS. Representative stepwise radiographs of the retrieval process executed in a swine model are shown below. Dashed circles indicate coupling of retrieval device with GRS. The components of both ends of the GRS [glue, a retainer, and a poly(ε-caprolactone) (PCL) plug] are also shown;

(FIG. 9A) Coated drug pills are made by mixing drug with silicones and extracting individual pills from the homogeneous matrix using a biopsy punch before spray-coating pills in a pan coater. A schematic visualization and a cross-sectional image of the Eudragit RS 100-coated doxycycline hyclate pill are shown. (FIG. 9B) In vitro release of doxycycline hyclate from a drug pill in SGF with formulations including different concentrations of PEG and Eudragit RS 100 coatings. (FIG. 9C) In vitro release of isoniazid from a drug pill in water. (FIG. 9D) In vitro release of ethambutol from a drug pill in SGF. (FIG. 9E) In vitro release of pyrazinamide from a drug pill in SGF. (FIG. 9F) In vitro release of moxifloxacin from a drug pill in SGF. (FIG. 9G) In vitro release of rifampicin in water from devices with 2 g of drug and 0% PEG. Inset: Image of the rifampicin-loaded device. Error bars represent SD for n=3 samples in each group;

FIGS. 10A-10D show in vivo release of doxycycline hyclate from the GRS in a swine model, according to one set of embodiments. (FIG. 10A) Representative photograph of a GRS after assembly of drug pills along a nitinol wire before deployment in vivo. (FIG. 10B) Representative photo of a retrieved GRS after 28 days in vivo in a swine model. (FIG. 10C) Left: Concentration-time profiles of doxycycline hyclate in serum after administering a single dose of 100 mg (n=3). Right: Concentration-time profiles of doxycycline hyclate in serum after administering the GRS, which had 10 g of drug across four formulations (n=3; FIG. S5). (FIG. 10D) Area under the curve (AUC) and the duration of drug release for a single dose compared to the formulations of the GRS administered in vivo, with the mean value and SD reported for n=3 samples in each group;

FIGS. 17A-17F shows field questionnaire results at TB clinics, according to one set of embodiments. (17A) Table of options presented to TB health care providers and patients with TB regarding four different methods of improving patient adherence to treatment. (17B) Responses from health care providers on how they would allocate rupees towards four different options to improve patient adherence to treatment. (17C) Responses from patients on whether each option would help them adhere to treatment. (17D) Table of options presented to TB health care providers and patients with TB regarding three different routes of administering a long-term gastric resident device for TB treatment. (17E) Responses from health care providers on the feasibility of three different routes of administration with respect to the time each option would take in a TB clinic. (F) Responses from patients on their willingness to try three different routes of administration for a long-lasting gastric resident device for TB treatment;

FIG. 24A is a schematic illustration of an exemplary system, according to one set of embodiments;

FIGS. 24B-24E are x-ray images of an exemplary retrieval system used to a retrieve a gastric residence system from the stomach of a subject, according to one set of embodiments;

FIG. 26A is photograph of a locking mechanism, according to one set of embodiments;

FIG. 26B is a plot of total impulse versus barb angle, according to one set of embodiments;

DETAILED DESCRIPTION

Drug delivery components and resident articles for gram-level dosing are generally provided. Retrieval systems and related methods are also provided.

In some embodiments, the articles are configured for transesophageal administration, transesophageal retrieval, and/or gastric retention to/in a subject. Advantageously, the articles described herein may comprise relatively high levels of drug loading and stability (e.g., greater than or equal to 1 gram), obtain gastric retention for relatively long periods of time, and/or may be compatible with a broad range of drug classes. In certain embodiments, the article includes dimensions configured for transesophageal administration with a gastric resident system. In some cases, the article may be configured to control drug release e.g., with zero-order drug kinetics with no potential for burst release for weeks to months. In some embodiments, the articles described herein comprise biocompatible materials and/or are safe for gastric retention. In certain embodiments, the article includes dimensions configured for transesophageal retrieval. In some cases, the articles described herein may comprise relatively large doses of drug (e.g., greater than or equal to 1 gram).

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans.

Figure 1A:
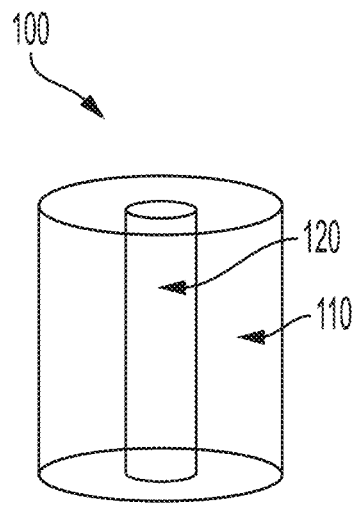
FIG. 1A is a schematic illustration of an exemplary article, according to one set of embodiments.

In some embodiments, the article comprises a polymer matrix (e.g., comprising a polymeric material) and a therapeutic agent associated with the polymer matrix. For example, as illustrated in FIG. 1A, exemplary article 100 comprises polymer matrix 110. In certain embodiments, article 100 comprises hollow core 120 disposed within polymer matrix 110. In some embodiments, the hollow core disposed within the polymeric matrix is configured to receive an elastic wire.

In certain embodiments, the therapeutic agent is disposed within the polymer matrix. In some embodiments, the therapeutic agent is adjacent the polymer matrix. As used herein, when a component is referred to as being "adjacent" another component, it can be directly adjacent to (e.g., in contact with) the component, or one or more intervening components also may be present. A component that is "directly adjacent" another component means that no intervening component(s) is present. In some cases, the therapeutic agent may be directly adjacent the polymer matrix (e.g., as a layer deposited on the polymer matrix).

In some embodiments, the polymer matrix comprises a plurality of holes (e.g., microdrilled holes in the polymer matrix). In some embodiments, the plurality of holes have an average diameter of greater than or equal to 0.1 mm, greater than or equal to 0.2 mm, greater than or equal to 0.5 mm, greater than or equal to 0.7 mm, greater than or equal to 0.8 mm, or greater than or equal to 0.9 mm. In certain embodiments, the plurality of holes have an average diameter of less than or equal to 1 mm, less than or equal to 0.9 mm, less than or equal to 0.7 mm, less than or equal to 0.5 mm, or less than or equal to 0.2 mm. Combinations of the above-referenced ranges are also possible (e.g., greater than or equal to 0.1 mm and less than or equal to 1 mm). Other ranges are also possible.

In certain embodiments, the polymeric matrix comprises a polymeric material. In some embodiments, the polymeric material is selected from the group consisting of vinylpolysiloxane, polydimethylsiloxane, polycaprolactone, polyethylene, polyethylene-vinyl acetate, methylcellulose, hydroxypropylmethylcellulose, hydroxypropylcellulose, hydroxyethylcellulose, ethylhydroxyethylcellulose, sodiumcarboxymethylcellulose, ethylcellulose, hypromellose acetate succinate, cellulose acetate, cellulose acetate propionate, and combinations thereof.

The polymeric material may have any suitable Young's elastic modulus. In some embodiments, the Young's elastic modulus of the polymeric material is less than or equal to 10 MPa, less than or equal to 8 MPa, less than or equal to 6 MPa, less than or equal to 4 MPa, less than or equal to 2 MPa, less than or equal to 1 MPa, or less than or equal to 0.8 MPa. In certain embodiments, the Young's elastic modulus of the polymeric material is greater than or equal to 0.5 MPa, greater than or equal to 0.8 MPa, greater than or equal to 1 MPa, greater than or equal to 2 MPa, greater than or equal to 4 MPa, greater than or equal to 6 MPa, or greater than or equal to 8 MPa. Combinations of the above-referenced ranges are also possible (e.g., greater than or equal to 0.1 MPa and less than or equal to 10 MPa). Other ranges are also possible.

In some embodiments, the article is selected to have a particular diameter e.g., suitable for transesophageal administration and/or transesophageal retrieval. In some embodiments, the article has a diameter of less than or equal to 20 mm, less than or equal to 15 mm, less than or equal to 10 mm, less than or equal to 8 mm, less than or equal to 6 mm, less than or equal to 4 mm, or less than or equal to 2 mm. In certain embodiments, the article has a diameter of greater than or equal to 1 mm, greater than or equal to 2 mm, greater than or equal to 4 mm, greater than or equal to 6 mm, greater than or equal to 8 mm, greater than or equal to 10 mm, or greater than or equal to 15 mm. Combinations of the above-referenced ranges are also possible (e.g., greater than or equal to 1 mm and less than or equal to 10 mm, greater than or equal to 1 mm and less than or equal to 20 mm). Other ranges are also possible.

In some embodiments, the article may have a particular maximum dimension (e.g., length) e.g., suitable for transesophageal administration and/or transesophageal retrieval. In some embodiments, the maximum dimension of the article is greater than or equal to 5 mm, greater than or equal to 8 mm, greater than or equal to 10 mm, greater than or equal to 15 mm, greater than or equal to 20 mm, greater than or equal to 25 mm, greater than or equal to 50 mm, greater than or equal to 100 mm, greater than or equal to 250 mm, greater than or equal to 500 mm, or greater than or equal to 750 mm. In certain embodiments, the maximum dimension of the article is less than or equal to 1000 mm, less than or equal to 750 mm, less than or equal to 500 mm, less than or equal to 250 mm, less than or equal to 100 mm, less than or equal to 50 mm, less than or equal to 25 mm, less than or equal to 20 mm, less than or equal to 15 mm, less than or equal to 10 mm, or less than or equal to 8 mm. Combinations of the above-referenced ranges are also possible (e.g., greater than or equal to 5 mm and less than or equal to 1000 mm). Other ranges are also possible.

In some embodiments, the article may comprise a coating (e.g., to reduce or eliminate the burst release of a drug from the surface of the article). In some cases, the coating is adjacent (e.g., directly adjacent) the polymer matrix. In certain embodiments, the coating is selected from the group consisting of Eudragit RS PO, Eudragit NM 30D, polycaprolactone, ethylcellulose, cellulose acetate, cellulose acetate butyrate, polydimethysiloxane, polivinylacetate, and vinylpolysiloxane. Other coatings are also possible.

In certain embodiments, the article may comprise an excipient. In some cases, the excipient may be used to tune (e.g., change) the release rate of the drug (e.g., as compared to an article without such excipient). In some embodiments, the excipient comprises polyethylene glycol and/or silicone oil. In some cases, the polyethylene glycol has a number average molecular weight of greater than or equal to 300 g/mol and less than or equal to 500,000 g/mol (e.g., greater than or equal to 400 g/mol and less than or equal to 3,350 g/mol, greater than or equal to 400 g/mol and less than or equal to 200,000 g/mol, greater than or equal to 3,350 g/mol and less than or equal to 200,000 g/mol). Other ranges are also possible.

In some embodiments, a magnetic component (e.g., a magnet) may be associated with an end (e.g., an end surface) of the article. Suitable magnetic materials include, for example, aluminum nickel cobalt alloys, ferrites, and neodymium-based materials. Such magnetic components may be useful for, for example, retrieval of the article (e.g., from a location internal to the subject). In certain embodiments, the article comprises a hollow core. In certain embodiments, the hollow core is configured to receive an elastic wire (e.g., comprising nitinol). In some embodiments, the elastic wire comprises a superelastic alloy and/or shape memory material.

According to some embodiments, the composition and methods described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. While much of the specification describes the use of therapeutic agents, other agents listed herein are also possible.

In a particular set of embodiments, the therapeutic agent is selected from the group consisting of doxycycline hyclate, moxifloxacin, pyrazinamide, ethambutol, isoniazid, rifampicin, Streptomycin, moxifloxacin, interferon, peginterferon, ribavirin, paritaprevir, simepravir, grazoprevir, ladispavir, ombitasvir, elbasavir, daclatasvir, and sofosbuvir. Other therapeutic agents are also possible. For example, agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals.

Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti(retro)viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, prostaglandins, antimicrobials (including antibiotics, antifungals, antivirals, antiparasitics), antimuscarinics, anxioltyics, bacteriostatics, immunosuppres sant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery article. These may be vitamins, supplements such as calcium or biotin, or natural ingredients such as plant extracts or phytohormones.

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell receptors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In certain embodiments, the therapeutic agent is present in the article in an amount greater than or equal to 1 gram, greater than or equal to 2 grams, greater than or equal to 3 grams, greater than or equal to 5 grams, greater than or equal to 10 grams, greater than or equal to 20 grams, greater than or equal to 30 grams, greater than or equal to 40 grams, greater than or equal to 50 grams, greater than or equal to 60 grams, greater than or equal to 70 grams, or greater than or equal to 80 grams, greater than or equal to 90 grams. In some embodiments, the therapeutic agent is present in the article in an amount of less than or equal to 100 grams, less than or equal to 90 grams, less than or equal to 80 grams, less than or equal to 70 grams, less than or equal to 60 grams, less than or equal to 50 grams, less than or equal to 40 grams, less than or equal to 30 grams, less than or equal to 20 grams, less than or equal to 10 grams, less than or equal to 5 grams, less than or equal to 3 grams, or less than or equal to 2 grams. Combinations of the above-referenced ranges are also possible (e.g., greater than or equal to 1 gram and less than or equal to 100 grams, greater than or equal to 2 grams and less than or equal to 100 grams, greater than or equal to 3 grams and less than or equal to 100 grams). Other ranges are also possible.

In some embodiments, the articles described herein comprises two or more types of therapeutic agents. For example, in some embodiments, a first therapeutic agent and a second therapeutic agent are present in the article such that the total amount of the first and second therapeutic agent is in one or more ranges described above (e.g., the total amount of therapeutic agent is greater than or equal to 1 gram and less than or equal to 100 grams). In some embodiments, each therapeutic agent is present in an amount such that the total amount of therapeutic agents is greater than or equal to 1 gram. In some embodiments, each therapeutic agent is present in an amount as described above (e.g., each therapeutic agent is present in an amount of greater than or equal to 1 gram and less than or equal to 100 grams).

In certain embodiments, the therapeutic agent is present in the article at a concentration such that, upon release from the article, the therapeutic agent elicits a therapeutic response.

In some embodiments, a subject may demonstrate health benefits, e.g., upon administration of the article.

In some embodiments, the article comprises a polymer matrix (e.g., polymeric material) having a reconfigurable shape. For example, in some embodiments, the article has a first shape/configuration (e.g., an elongated (e.g., straight) shape) and, upon removal of an elastic wire, obtains a second shape/configuration (e.g., a coil), different than the first shape.

The polymer matrix may be reconfigured, in some cases, into a shape such as a straight shape, a J-hook shape, a spherical shape, a cylindrical shape, a coil shape, or a toroidal shape. Other shapes are also possible. In some embodiments, the polymeric material is reconfigured upon insertion or removal of an elastic wire (e.g., from a hollow core of the polymer matrix). In some embodiments, the reconfigured shape is such that the article may be retained (e.g., at a location internal to a subject) as described in more detail herein. In some embodiments, the reconfigured shape has dimension incompatible with passage through proximal and/or distal orifices of a containing viscus of a subject (e.g., such that the article is retained).

In some embodiments, the article has a maximum dimension (e.g., length when elongated) of greater than or equal to 20 cm, greater than or equal to 28 cm, greater than or equal to 30 cm, greater than or equal to 50 cm, greater than or equal to 100 cm, greater than or equal to 200 cm, or greater than or equal to 500 cm. In certain embodiments, the article has a maximum dimension of less than or equal to 1000 cm, less than or equal to 500 cm, less than or equal to 200 cm, less than or equal to 100 cm, less than or equal to 50 cm, less than or equal to 30 cm, or less than or equal to 28 cm. Combinations of the above-referenced ranges are also possible (e.g., greater than or equal to 20 cm and less than or equal to 1000 cm, greater than or equal to 20 cm and less than or equal to 200 cm). Other ranges are also possible.

In some embodiments, the article has a size and/or configuration such that the article does not fit inside a standard capsule (e.g., a capsule having a shape or size as described in the USP including, but not limited to, 000 capsule, 00 capsule, 0 capsule, 1 capsule, 2 capsule, 3 capsule, 4 capsule, or 5 capsule). That is to say, in some embodiments, the article is not configured to be delivered in a capsule. As described herein, in some embodiments, the article is configured to be administered transesophageally.

In some embodiments, the shape of the polymeric material is configured to be reconfigured such that the article has a maximum overall diameter (e.g., in the second configuration) of greater than or equal to 2 cm, greater than or equal to 5 cm, greater than or equal to 10 cm, or greater than or equal to 25 cm. In certain embodiments, the shape of the polymeric material is configured to be reconfigured such that the article has a maximum overall diameter of less than or equal to 50 cm, less than or equal to 25 cm, less than or equal to 10 cm, or less than or equal to 5 cm. Combinations of the above-referenced ranges are also possible (e.g., greater than or equal to 2 cm and less than or equal to 50 cm, greater than or equal to 10 cm and less than or equal to 25 cm). Other ranges are also possible.

In certain embodiments, the article is configured to be retained at a location internal to a subject for a relatively long period of time. For example, in some embodiments, the article is retained at the location internal to the subject for at least about 1 day, at least about 3 days, at least about 7 days, at least about 2 weeks, at least about 1 month, at least about 2 months, at least about 6 months, at least about 1 year, or at least about 2 years. In certain embodiments, the article is retained at the location internal to the subject for less than or equal to about 3 years, less than or equal to about 2 years, less than or equal to about 1 year, less than or equal to about 1 month, less than or equal to about 1 week, or less than or equal to about 3 days. Combinations of the above-referenced ranged are also possible (e.g., between about 24 hours and about 3 years, between about 1 week and 1 year, between about 1 year and 3 years). Other ranges are also possible.

In some embodiments, the article may be designed and configured to have a relatively low force of administration (e.g., the force required to administer the device through a nasogastric or endoscopic tube). In certain embodiments, the article has an administration force of less than or equal to 20 N, less than or equal to 10 N, less than or equal to 5 N, or less than or equal to 1 N. In some embodiments, the article has an administration force of greater than or equal to 0.1 N, greater than or equal to 1 N, greater than or equal to 5 N, or greater than or equal to 10 N. Combinations of the above-referenced ranges are also possible (e.g., greater than or equal to 0.1 N and less than or equal to 20 N). Other ranges are also possible.

In some embodiments, the polymeric material may be encapsulated (e.g., by an elastomeric hollow tube).

In some embodiments, the location internally of the subject is the colon, the duodenum, the ileum, the jejunum, the stomach, or the esophagus.

Retrieval systems and related methods (e.g., for gastric resident articles) are also provided. In some embodiments, the retrieval system is configured to be administered transesophageally to a location internal to a subject such that a gastric residence system (e.g., one or more articles and/or components described herein), located at the location internal to the subject, may be retrieved (e.g., removed from the subject). Advantageously, the systems described herein may be small enough to be fit through the esophagus of a subject to non-invasively access the stomach and/or may be operated without the use of endoscopy and/or imaging (e.g., x-ray imaging). In some cases, the systems described herein may be configured to sense (e.g., via a sensor associated with the system) one or more gastric resident devices present in the subject. In some embodiments, upon detection of the gastric resident system, the retrieval system outputs a contact signal (e.g., via the sensor) such that a user may retrieve the device. In certain embodiments, the system may be configured to contact and bind with the gastric resident system (e.g., while able to hold the weight of the gastric resident system and retrieve it through the esophagus of the subject).

In some embodiments, the system comprises a polymeric component having a flexible member and a binding component associated with an end portion of the polymeric component. In some embodiment, the polymeric component comprises a flexible tube.

In some embodiments, the system may be administered transesophageally to a subject. In certain embodiments, the system comprises a sensor associated with an end portion of the polymeric component. In some cases, the sensor may be used to determine a distance between the binding component and the gastric residence system present at the location internal to the subject. The sensor may be, in some cases, adjacent (e.g., directly adjacent) an end portion of the polymeric component.

In some embodiments, upon administration of the retrieval system to the location internal to the subject, the retrieval system may interface, via a locking mechanism associated with an end portion of the polymeric component, with the gastric residence system. The locking mechanism may be, in some cases, adjacent (e.g., directly adjacent) an end portion of the polymeric component. In certain embodiments, after interfacing with the gastric residence system, the gastric residence system may be removed (e.g., via the retrieval system) from the location internal to the subject. In some embodiments, the system is configured to maintain contact (e.g., via the binding mechanism, via the locking mechanism) with the gastric residence system during extraction of said gastric residence system from a location internal to a subject.

In certain embodiments, the binding component comprises a magnet. In some such embodiments, the system is configured to magnetically associate (e.g., bind) with a gastric residence system.

In some embodiments, the binding component comprises a first species configured to interact with a second species via a binding event.

In some embodiments, the first species of the binding component interacts with a second species via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups. For example, the species may include a functional group, such as a thiol, aldehyde, ester, carboxylic acid, hydroxyl, and the like, wherein the functional group forms a bond with the nanodiamond particle. In some cases, the species may be an electron-rich or electron-poor moiety wherein interaction between the first species and the second species comprises an electrostatic interaction.

In some cases, the first species of the binding component may comprise a biological or a chemical group capable of binding another biological or chemical molecule. For example, the first species may include a functional group, such as a thiol, aldehyde, ester, carboxylic acid, hydroxyl, and the like, wherein the functional group forms a bond with the second species.

In some embodiments, the first species and the second species interact via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of species include peptides, proteins, DNA, RNA, PNA. Other species and binding pairs are also possible.

In some embodiments, the sensor is configured to determine a distance between the binding component and the gastric residence system. For example, the sensor may be configured to determine, in some cases, the distance between a magnetic component associated with the retrieval system and a magnet associated with the gastric residence system. In a particular set of embodiments, the sensor is a Hall effect sensor. Other sensors are also possible.

As described above and herein, in some embodiments, the system comprises a locking mechanism (e.g., for anchoring the gastric residence system to the retrieval system). In certain embodiments, the locking mechanism comprises a snare. In some embodiments, the locking mechanism comprises a plurality of barbed features (e.g., barbs).

In some embodiments, the system is configured to pass through a nasogastric and/or endoscopic tube. For example, in certain embodiments, the system has a maximum diameter less than or equal to 7 mm, less than or equal to 6.5 mm, less than or equal to 6 mm, less than or equal to 5 mm, less than or equal to 4 mm, less than or equal to 3 mm, or less than or equal to 2.5 mm. In some embodiments, the system has a maximum diameter of greater than or equal to 2 mm, greater than or equal to 2.5 mm, greater than or equal to 3 mm, greater than or equal to 4 mm, greater than or equal to 5 mm, greater than or equal to 6 mm, or greater than or equal to 6.5 mm. Combinations of the above-referenced ranges are also possible (e.g., less than or equal to 7 mm and greater than or equal to 2 mm). Other ranges are also possible.

In some embodiments, the gastric residence systems described herein may comprise one or more features and/or articles described in a co-owned U.S. Provisional Patent Application Ser. No. 62/678,471, filed May 31, 2018, and entitled "RESIDENT ARTICLES FOR GRAM-LEVEL DOSING," and/or in a co-owned U.S. Provisional Patent Application Ser. No. 62/678,492, filed May 31, 2018, and entitled "DRUG DELIVERY ARTICLES FOR GRAM-LEVEL DOSING," and/or in a co-owned U.S. Provisional Patent Application Ser. No. 62/817,477, filed Mar. 12, 2019, and entitled "DRUG DELIVERY ARTICLES FOR GRAM-LEVEL DOSING," each of which is incorporated herein by reference in its entirety.

In some embodiments, the location internally of the subject is the colon, the duodenum, the ileum, the jejunum, the stomach, or the esophagus.

EXAMPLES

The following examples are intended to illustrate certain embodiments described herein, including certain aspects of the present invention, but do not exemplify the full scope of the invention.

The following examples, in some or all of the examples, demonstrate drug delivery formulations combined with a gastric resident article capable of e.g., one-time administration through a nasogastric or endoscopic tube, safe retention in the gastric cavity, 2 weeks of drug release, and/or one-time transesophageal retrieval through a nasogastric or endoscopic tube. The drug delivery formulations may have features including, for example, 1) attachment to a superelastic wire, 2) homogenous dispersion of the drug, 3) made of biocompatible components, 4) maintain stability of the drug form once formulated, and/or 5) have an outer diameter less than 20 French (6.667 mm) in diameter to fit within a nasogastric tube.

The following examples, in some or all of the examples, demonstrate articles capable of one-time administration and retrieval, extended residence, and/or release of pharmacologically active therapies for weeks to months with a holding capacity of more than 10 grams of active pharmaceutical ingredient (API). Gastric retention in vivo with durable residence times has been demonstrated. High levels of drug loading and stability were achieved. Such article could serve as a platform to maximize adherence to a broad range of drugs.

In some examples, the article consisted of a series of shapes with the capacity for holding at least 10 grams of API and therefore at least 28.66 cm in length but also compatible with one-time transesophageal administration, effective gastric retention, and one-time transesophageal retrieval. The devices can be, in some cases, delivered and retrieved via a nasogastric or endoscopic tube, which is inserted into the stomach by the nose and is advantageous to use for one-time administration and retrieval of the device.

The article may be small enough to be fit through the esophagus of a patient to non-invasively access the stomach, able to adopt a shape in the gastric cavity large enough to prevent passage through the pylorus, comprise high levels of drug loading, and/or include controlled drug release with no potential for burst release. In some examples, the drug is stable in the hostile gastric environment for extended duration. The article may be capable of degrading into forms which have no potential for intestinal obstruction and which can readily pass or be retrieved once the drug has been released from the device.

The following examples, in some or all of the examples, describe articles having shapes that are safe transesophageal administration, safe for retention in the gastric cavity, are capable of holding greater than or more than 10 grams of API, and/or are safe transesophageal retrieval.

The following examples, in some or all of the examples, demonstrate a retrieval system capable of safely being administered through a nasogastric or endoscopic tube, sensing a gastric resident drug delivery device, and/or retrieving it via a nasogastric or endoscopic tube. In some cases, the retrieval system has one or more of the following components: 1) a Hall effect sensor for detection of the gastric resident device, 2) an output of the Hall effect sensor, and 3) a magnet to contact the gastric resident system and facilitate retrieval. The sensor is incorporated, for example, to provide distance-correlated analog sensing of the magnetic field output by magnets in the gastric resident system. The three pins of the sensor may be soldered to wires that are then connected to a breadboard for power and display of the distance to the magnets. The entire system is designed to ensure safe passage through the nasogastric tube (e.g., an outer diameter of the system is less than 20 French (6.667 mm) in diameter and at least 2 feet in length to reach the stomach.)

In some examples, the system includes one or more of the following features: 1) such a system may be small enough to be fit through the esophagus of a patient to non-invasively access the stomach; 2) such a system may sense the gastric resident system without using endoscopy or imaging; 3) upon detection of the gastric resident system's magnet, the retrieval system may output a contact signal to the user retrieving the system; and 4) the system may make contact with the gastric resident system while able to hold the weight of the gastric resident system and retrieve it through the esophagus of the patient.

Example 1

Figure 1B:
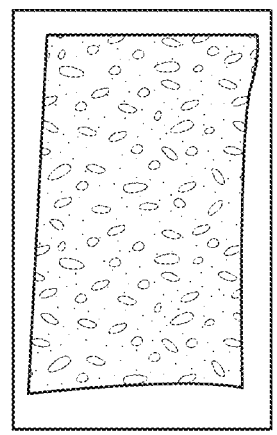
FIG. 1B shows an exemplary article, according to one set of embodiments.
Figure 1C:
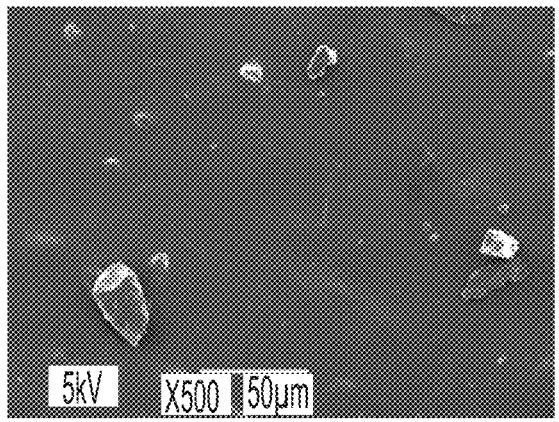
FIG. 1C shows a scanning electron microscopy image of drug crystals on the surface of an exemplary article, according to one set of embodiments.
Figure 1D:
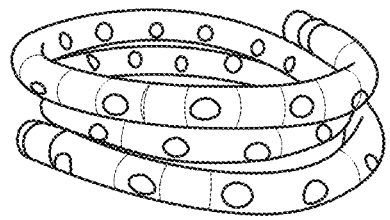
FIG. 1D shows an exemplary article, according to one set of embodiments.

Cylindrical pills of drug were mixed with vinylpolysiloxane with height greater than 5 mm and diameter of 4 mm. They had a hollow core (e.g., hole) with diameter 0.5 mm in the middle to allow a superelastic wire to fit inside. The model drug, doxycycline hyclate, is added to the Zhermack Elite Double 22 base and catalyst to obtain a final drug loading percentage of 32%. Each pill has around 30 mg of drug (FIG. 1B). Drug crystals less than 75 µm can be visualized on the surface of the pill using scanning electron microscope (FIG. 1C). A series of pills with 0.5 mm holes inside them can be strung on a retention frame such as nitinol superelastic wire and encased in a Tygon tubing with stainless steel beads and Nusil glue at the ends of the article (FIG. 1D). Other drugs such as moxifloxacin, isoniazid, pyrazinamide, and ethambutol can also be mixed with the Zhermack Elite Double 22 base and catalyst at drug loading percentages greater than 25 wt %. Stability of the drug form can be evaluated using proton nuclear magnetic resonance spectroscopy after extraction of the drug from the matrix in water.

Figure 2A:
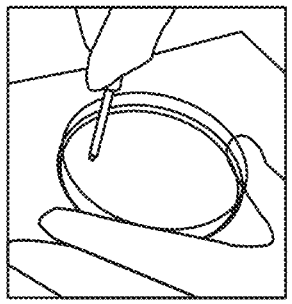
FIG. 2A shows an exemplary formation of an exemplary article, according to one set of embodiments.
Figure 2B:
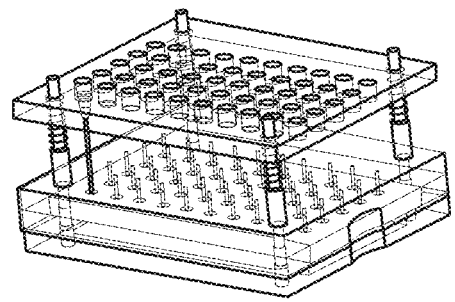
FIG. 2B shows an exemplary setup for forming an exemplary article, according to one set of embodiments.
Figure 2C:
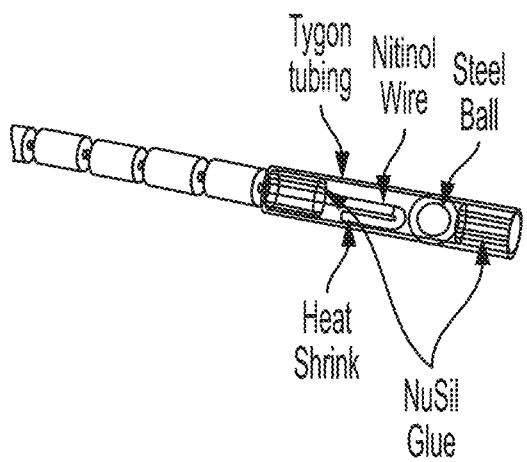
FIG. 2C shows an exemplary article, according to one set of embodiments.

The pills were created by first mixing the drug into the Zhermack Elite Double 22 base and catalyst. Other excipient polymers, such as polyethylene glycol, were also added in desired amounts as powders to tune the drug release. Drug loading percentages were determined relative to the finally cured silicone mixture weight. The silicone, drug, and excipient mixture were mixed at 1800 rpm for 30 seconds using the SpeedMixer™ DAC 150.1 FVX-K from Hauschild, Germany. The viscous uniform blend was poured into a polystyrene Petri dish, and individual pills were extracted using a 4 mm Miltex disposable biopsy punch (FIG. 2A). A custom fixture with 25 Gauge needles was used to core out a 0.5 mm hole in a series of 50 pills (FIG. 2B). The nitinol wire was inserted into the holes of the pills, and the ends of the wire were engulfed in 0.024 inch diameter heat-shrink tubing and inserted into a 2 inch piece of Tygon tubing (I.D.×O.D.: 3/16×0.25 in.). The end of the tubing was filled with Med3-4213 silicon adhesive from Nusil followed by a ¼ inch stainless steel ball bearing pressed in. More silicone adhesive was filled behind the ball bearing to completely seal the tubing and lock in the nitinol (FIG. 2C).

Flexible tubing can be surrounding all the pills with biopsy-punched or drilled holes in the tubing to allow stomach acid to reach the drug/siloxane pills. The ends of the nitinol wire may be sealed using glue or molten polymers such as Ellastolan or polycaprolactone.

Excipients can be added to the drug/siloxane matrix to tune the rate of release. For example, polyethylene glycol (PEG) 3350 can be added to increase the rate of release (FIG. 3A). Other molecular weights of PEG can also enable the same trend of increasing the release rate as more PEG is added.

The choice of matrix polymer can be vinylpolysiloxane, like the Zhermack Elite Double 22 base and catalyst, or it can be other polymers such as polydimethylsiloxane, polycaprolactone, polyethylene, or polyethylene-vinyl acetate. One article can have a combination of a variety of matrix system formulations with different excipients to tune the rate of drug release.

After deployment of the drug delivery formulations in three Yorkshire pigs in a large animal model, concentrations of doxycycline hyclate in the blood were measured, and drug release is sustained for at least 7 days with non-zero values (FIG. 3B).

Example 2

Coated cylindrical pills (articles) comprising drug and mixed with vinylpolysiloxane with height between 3-4 mm and diameter of 4 mm. They had with a hole with diameter 0.5 mm in the middle to allow a superelastic wire to fit inside. The model drug, doxycycline hyclate, was added to the Zhermack Elite Double 22 base and catalyst to obtain a final drug loading percentage of 32%. The uncoated pill is shown on the left in FIG. 4A, and the coated pill is shown on the right in FIG. 4B. The coatings help, for example, to prevent the burst release of drug from the surface of the pill. A library of coatings has been applied to the pills using a E91 airbursh and conventional pan coater attached to a Ewreka 403 unit: Eudragit RS PO, Eudragit NM 30D, polycaprolactone, ethylcellulose, cellulose acetate, cellulose acetate butyrate (CAB), polydimethysiloxane (PDMS), and vinylpolysiloxane (VPS).

A series of coated pills with 0.5 mm holes inside them can be strung on a retention frame such as nitinol superelastic wire and encased in a Tygon tubing with stainless steel beads and Nusil glue at the ends of the article (FIG. 1D). Other drugs such as moxifloxacin, isoniazid, pyrazinamide, and ethambutol can also be mixed with the Zhermack Elite Double 22 base and catalyst at drug loading percentages greater than 25 wt %. Pills of those drugs can also be coated using a conventional pan coater and airbrush.

The pills were created following the same procedure in Example 1. The coating solutions are dyed with red food coloring powder or iron oxide to visualize them around the green doxycycline hyclate/siloxane matrix. FIG. 4B shows a 149 μm Eudragit NM 30D coating, and FIG. 4C shows a 174 μm Eudragit RS PO coating. Other coatings, such as cellulose acetate butyrate, cellulose acetate, and PDMS have been described and developed elsewhere.

Articles with a series of 30 pills were made so that there was 1 gram of doxycycline hyclate in 2 grams of vinylpolysiloxane. Pills were coated with either cellulose acetate butyrate (CAB) or with Eudragit RS PO. A control with no coatings was also made. The articles were immersed in simulated gastric fluid, and the cumulative release of doxycycline hyclate was measured for more than 26 days. The articles with coatings, CAB and Eudragit RS PO, prevented the burst release in the first couple days (FIG. 4D). Drug release was achieved for more than 26 days.

Figure 5A:
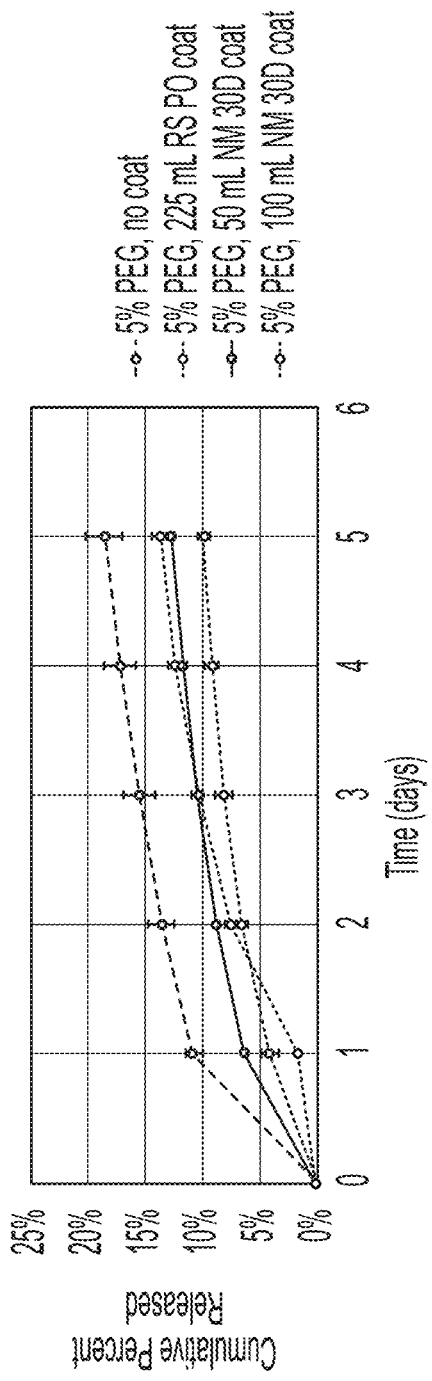
FIG. 5A is a plot of cumulative percent drug released versus time (days), according to one set of embodiments.
Figure 5B:
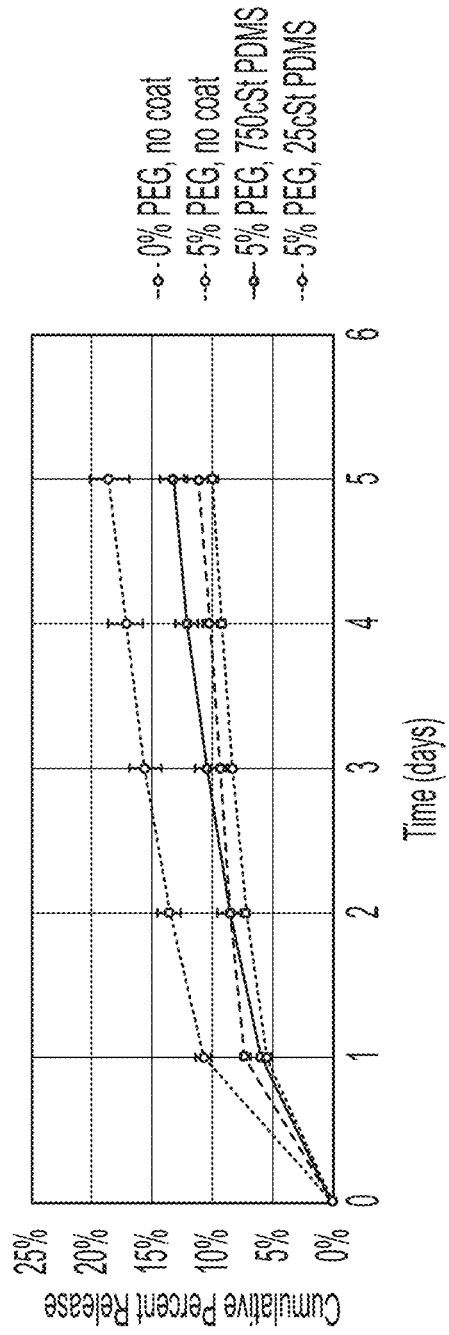
FIG. 5B is a plot of cumulative percent drug released versus time (days), according to one set of embodiments.

PEG 3350 was added to the matrix, and the effect of coatings Eudragit RS PO and Eudragit NM 30D coatings is shown in FIG. 5A. The coated pills prevented the burst release in the first day, and then the thicker coating of Eudragit NM 30D had a slower rate of release. Thickness of coatings was tuned by increasing the spray volume. PDMS with different viscosities (750 cst and 25 cst) were applied as a coating to the pills and also blunted the burst release and slowed down the release rate (FIG. 5B).

Example 3

Figure 6:
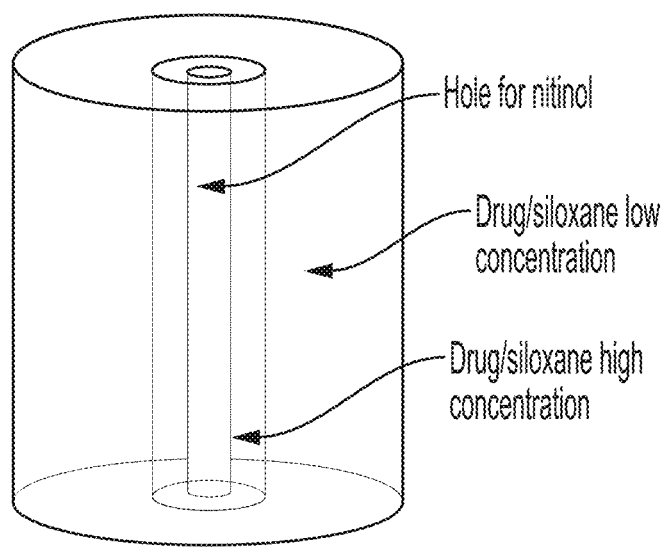
FIG. 6 is a schematic illustration of an exemplary article, according to one set of embodiments.

In another implementation shown in FIG. 6, a multi-matrix pill can be made with different layers of drug/matrix concentrations. The multi-matrix pill has a series of concentric cylinders with the outermost cylinder having a diameter of 4 mm and height of more than 5 mm. To prevent the burst release, the outer layer of the pill can have a low concentration of drug relative to the matrix material. The next layer moving inwards can have a higher concentration of drug relative to the matrix. Then, there must be a 0.5 mm hole for the retention frame superelastic wire like nitinol to pass. The multi-matrix pill could have many such layers with a gradient of drug concentrations starting with low to high from the outer surface of the pill to the inside. FIG. 4D shows the multi-matrix pill reducing the burst release and release rate of doxycycline hyclate. The multi-matrix pills can also be coated further using the coating described in Example 2.

Example 4

Figure 7:
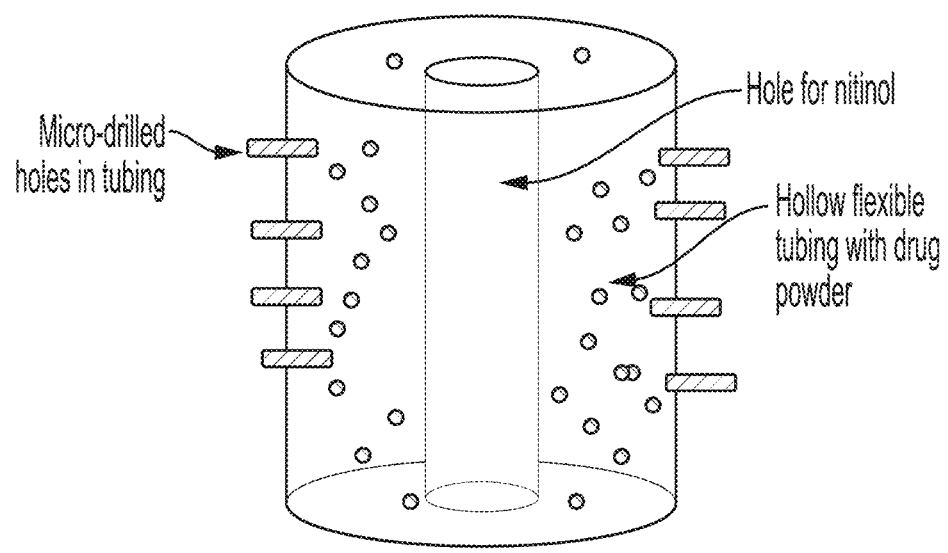
FIG. 7 is a schematic illustration of an exemplary article, according to one set of embodiments.

FIG. 7 shows another drug delivery system made of pills made of hollow tubing sealed with adhesive on the ends. Outer diameter of tubing is ¼ inch, and the inner diameter is 3/16 inch. The length of the tubing is more than 5 mm and it has drug powder in it. Drug release can occur by diffusion through micro-drilled or laser-cut holes in the tubing. These holes can be coated with polymer films that degrade at different times or are porous to control the rate of drug release. The nitinol wire can pass through the packed drug powder and connect multiple series of these pills.

Example 5

Design of a Gastric Residence System (GRS) for Multigram Dosing

Figure 8A:
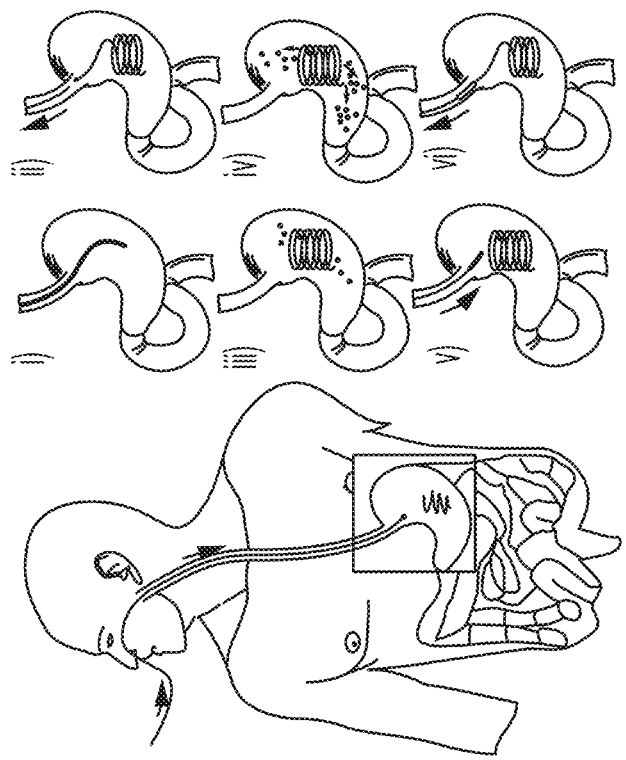
FIGS. 8A-8D show the design and in vivo evaluation of a large-dose gastric residence system (GRS) for drug delivery, according to one set of embodiments.
Figure 8B:
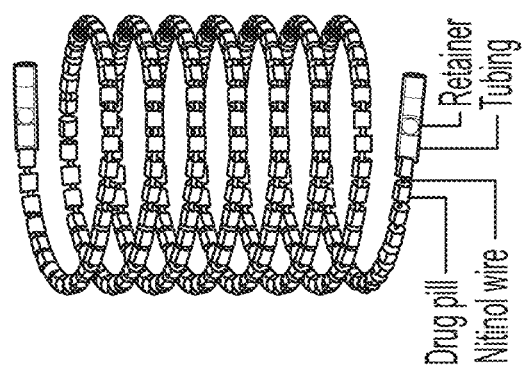

A large-dose GRS for long-term treatment, in some embodiments, is designed to (i) have a size and shape that can fit through the esophagus of a patient to non-surgically access the stomach, (ii) have the ability to adopt an alternative conformation in the stomach that prevents passage through the pylorus, (iii) achieve high concentrations of drug loading, (iv) be composed of biocompatible materials that are stable for an extended duration in the acidic gastric environment, (v) have no potential for gastrointestinal obstruction or perforation, and/or (vi) either be able to degrade into forms that can safely pass or be retrieved after the drug has been released from the device. Here, a GRS was designed that could be administered through an NG tube, which is inserted via the nose to access the stomach. After reaching the stomach, the GRS forms a cylindrical coil and continually releases grams of drug over the course of weeks, whereupon the device is retrieved back through an NG tube (FIG. 8A). The assembled GRS consisted of a superelastic nitinol wire as the retention frame upon which drug pills are strung with a retainer and tubing at the ends of the device (FIG. 8B). To tailor the drug loading and duration of therapy, the length of the GRS and formulation of drug pills may be modified (FIGS. 11A-11D).

Figure 8C:
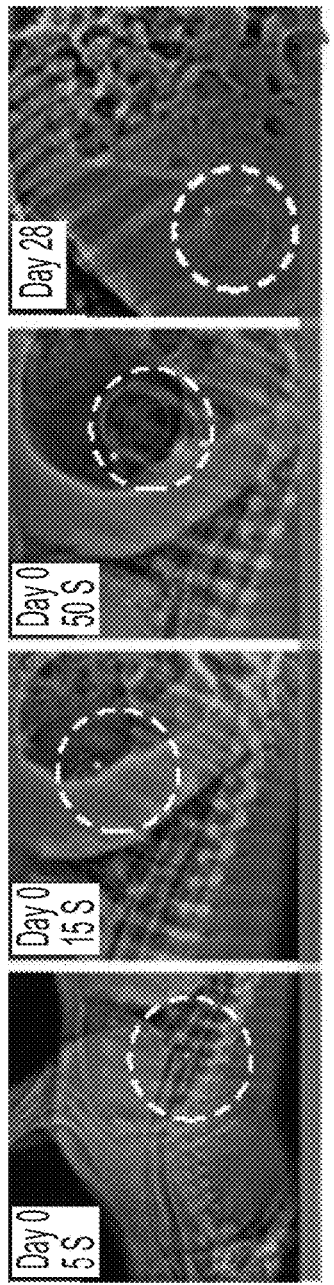
Figure 12:
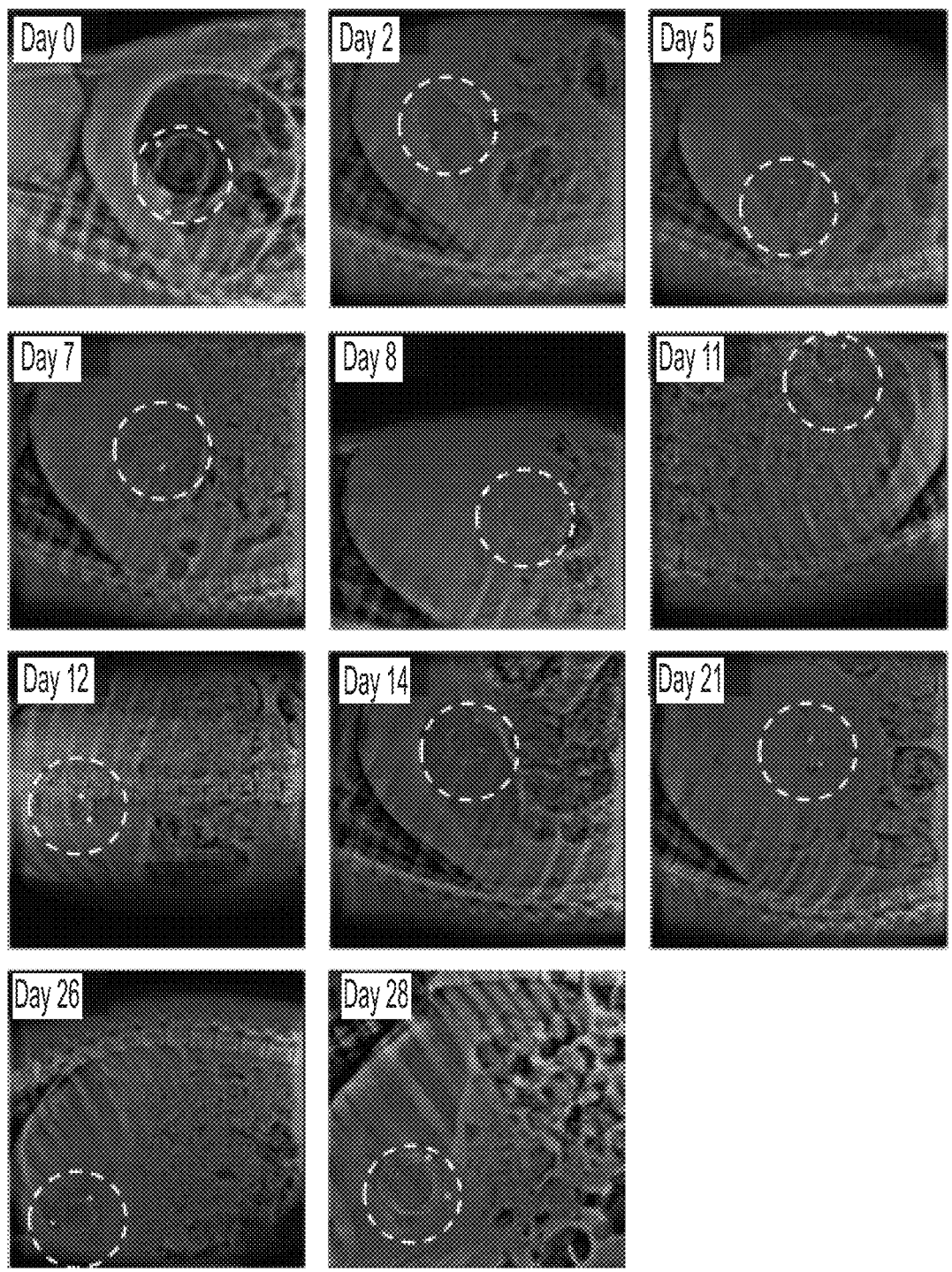
FIG. 12 shows serial radiographs of the GRS over 1 month in a swine model, according to one set of embodiments. Radiographs of the gastric cavity were taken every few days over the course of 1 month to monitor for safe long-term gastric residence of the GRS. The dotted lines encircle the GRS in the gastric cavity of the swine.
Figure 13A:
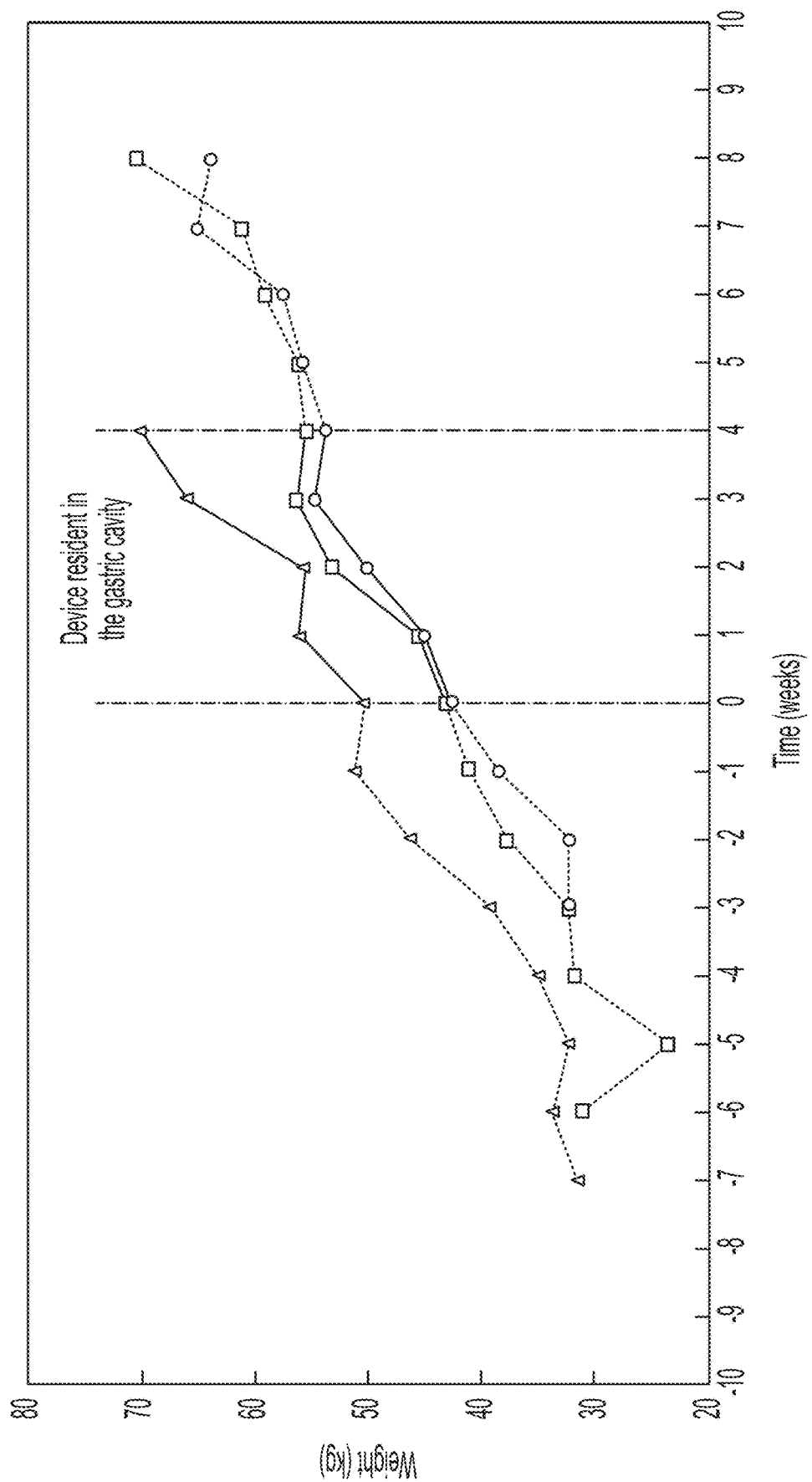
FIGS. 13A-13C shows effect of the GRS on the weight and stomach tissue of swine, according to one set of embodiments. (13A) The animals' weight was measured every week from when it was brought into the animal facility until when it was euthanized. Week 0 denotes the week that the GRS was administered to the gastric cavity of the animal. At the end of week 4, the GRS was retrieved from the gastric cavity, and the animal is either euthanized immediately or is used for other studies with the weight being measured every week. (13B) After 2 weeks of gastric residence for the GRS, the stomach mucosa was assessed for any damage. A representative hematoxylin and eosin stain of stomach tissue at week 0 (prior to deployment of the GRS) and at week 2 (when the GRS is retrieved and the animal is euthanized) is shown (n=3). (13C) Representative macroscopic image of the stomach tissue at the end of week 2 when a GRS was retrieved from the gastric cavity and the animal is euthanized to assess any damage to the mucosa (n=3)
Figure 13B:
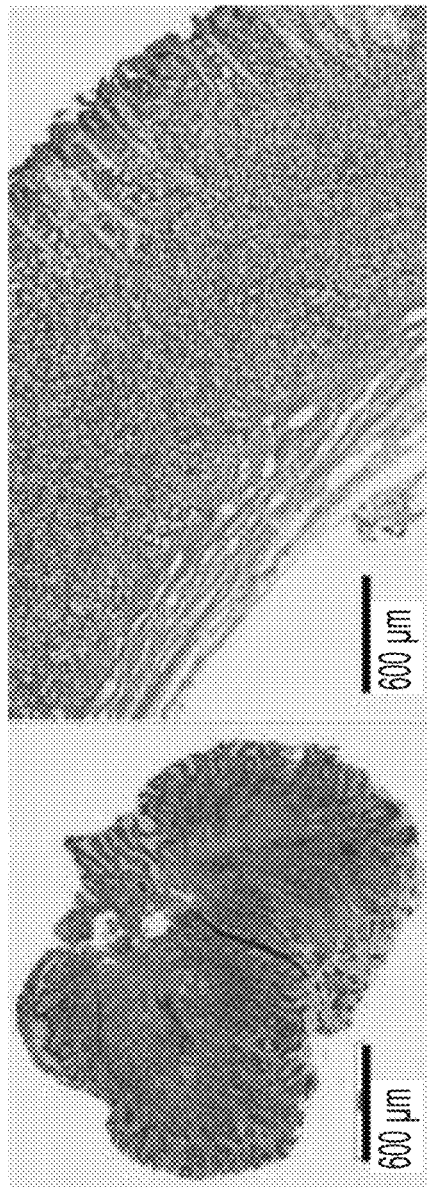
Figure 13C:
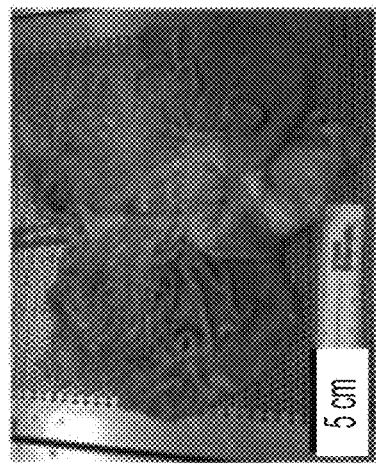

A coiled nitinol wire inside tubing was deployed to the gastric cavity of 30- to 75-kg Yorkshire pigs to demonstrate transesophageal administration and safe gastric retention in vivo. Yorkshire pigs generally have similar gastric anatomy to humans and have been previously used to evaluate long-acting drug delivery platforms. Representative serial abdominal radiographs during device deployment and month-long residence revealed the feasibility of the GRS to pass through the esophagus and form a coil in the stomach within 50 s (FIG. 8C). Without wishing to be bound by theory, the GRS was able to curl back into its original coil shape in the gastric cavity after passing through the esophagus because of, for example, the superelasticity of nitinol. Safe long-term gastric residence was evaluated by serial radiographs obtained over the course of 1 month and through endoscopic evaluation (FIG. 8C and FIG. 12). Even after prolonged gastric residence of these large devices, mucosal surfaces of the animals' stomachs did not show injury, erosions, or ulcerations; in addition, the animals did not show any weight loss, evidence of GI obstruction, or limitation in the passage of food or liquid (FIGS. 13A-13C).

Figure 8D:
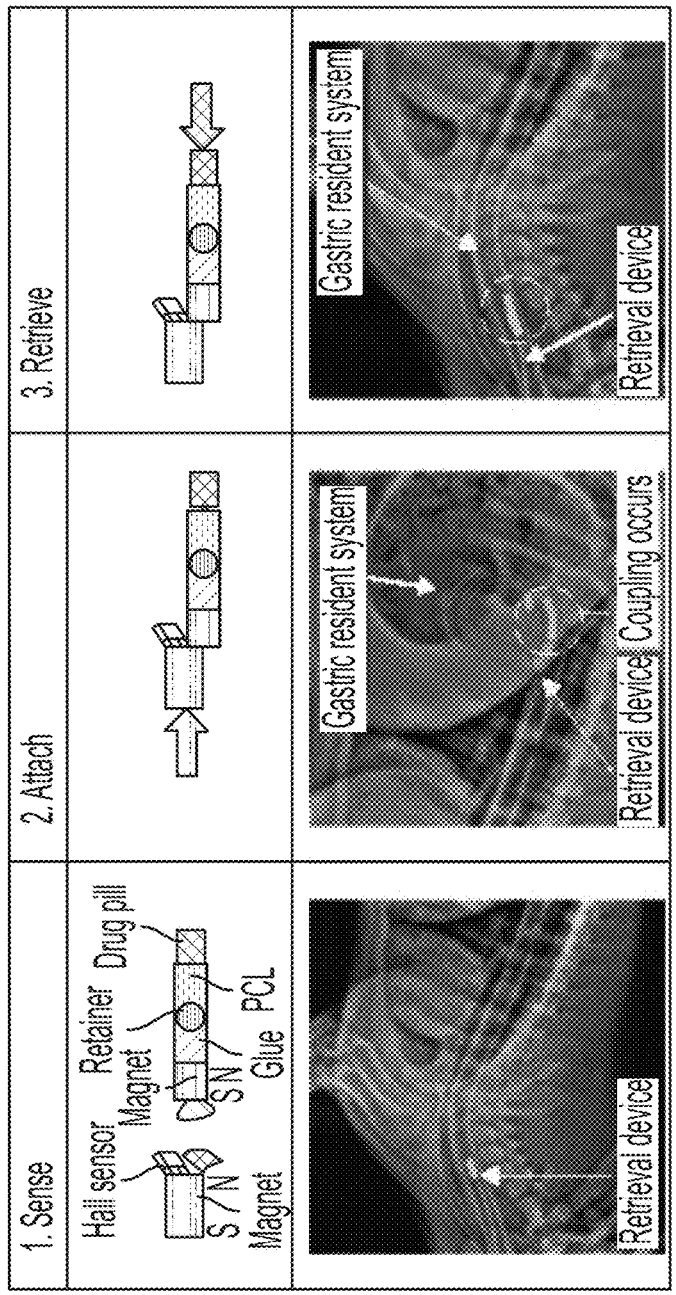
Figure 9A:
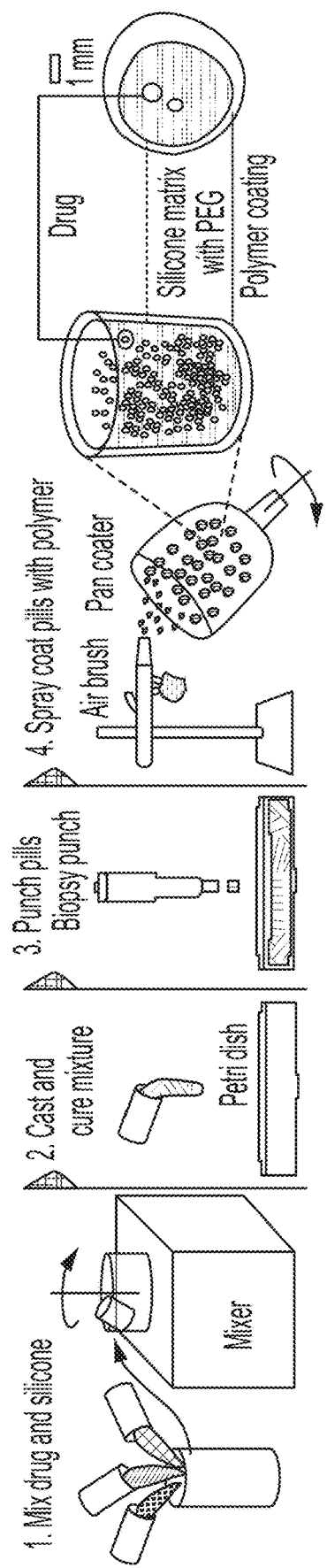
FIGS. 9A-9G show fabrication and in vitro release of TB antibiotics from individual drug pills, according to one set of embodiments.
Figure 14B:
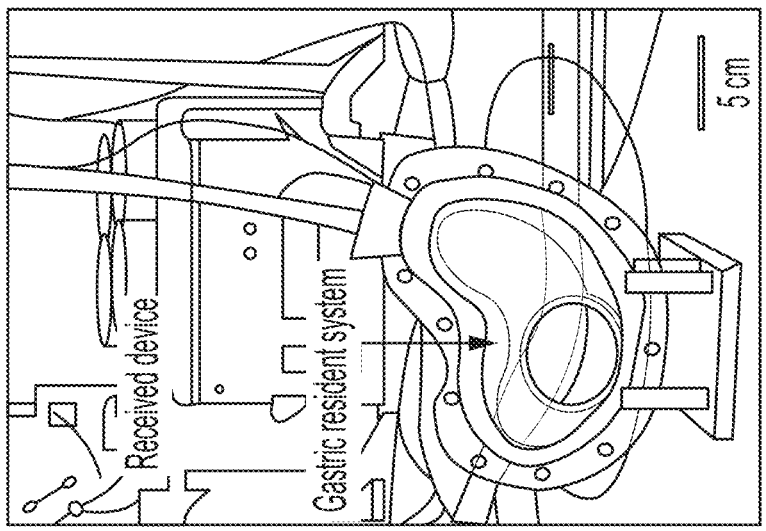
FIGS. 14A-14B shows hall effect sensor acid stability and retrieval using an in vitro stomach model, according to one set of embodiments. (14A) Voltage reading of the Hall effect sensor before and after submersion in simulated gastric fluid. Error bars represent the standard deviation for n=3 samples in each group. (14B) Photograph of a three-dimensional printed stomach model used to test sensing and magnetic attachment of the retrieval device to the gastric resident system.
Figure 14A:
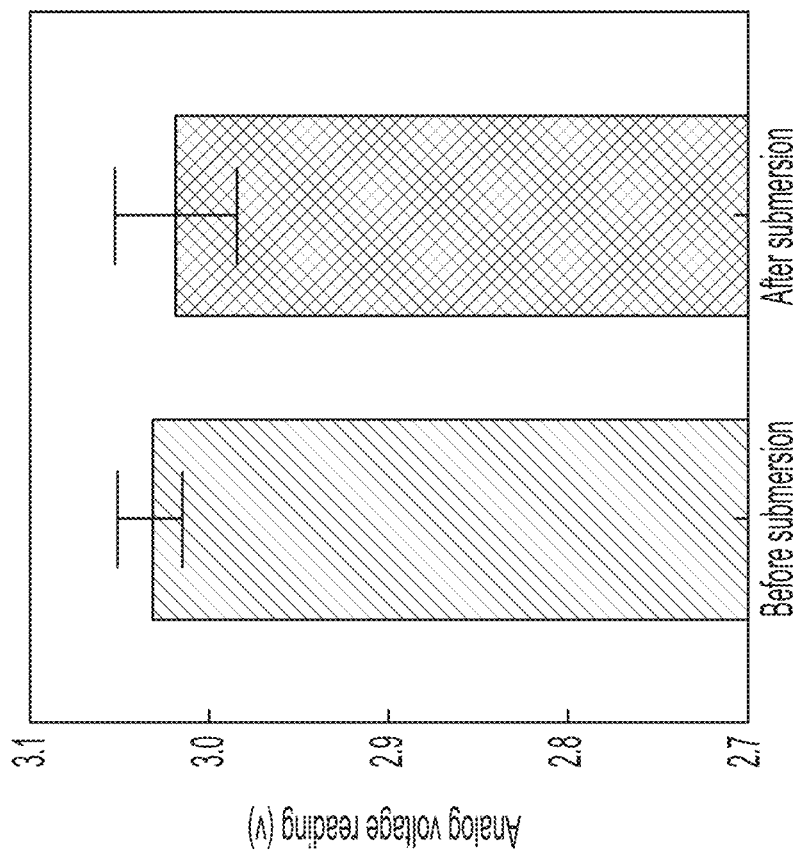

The GRS was designed to be retrieved through an NG tube after the release of the drug payload in the gastric cavity. The retrieval device consisted of a Hall effect sensor to determine the distance between a magnet on the end of the GRS and a magnet at the end of retrieval device (FIG. 8D). To ensure the stability of the Hall effect sensor in a low pH environment, it was placed in simulated gastric fluid (SGF) for 90 min; the measured voltage was comparable to the voltage measured in air before immersion in SGF (FIG. 14A). A three-dimensional (3D) printed in vitro human stomach model was constructed to test the feasibility of the retrieval procedure (FIG. 14B). A magnet was placed on each end of the GRS to maximize likelihood of retrieval. In vivo demonstration of GRS retrieval was successful, as demonstrated by representative serial radiographs (FIG. 8D). Thus, the potential of the GRS to be safely administered, to reside safely in the gastric cavity for 1 month, and to be retrieved through the esophagus, was demonstrated.
Controlled Drug Release with Coated Drug-Matrix Pills Pills of a single drug mixed were fabricated inside a silicone matrix and encapsulated each pill in a polymer coating to enable tailored dosing of each drug (FIG. 9A). Vinylpolysiloxane (VPS) was selected as a drug release matrix because of its flexibility, rapid curing time, and low-temperature mixing process with drug. A 300-μm-thick Eudragit RS 100 polymer coating was spray coated to help prevent the burst release of drug from the surface of the matrix. Each pill had a height and diameter of 4 mm with a 0.5-mm hole in the center through which to pass the nitinol wire and contribute to the assembled GRS (FIG. 9A).

Figures 9B, 9C, 9D:
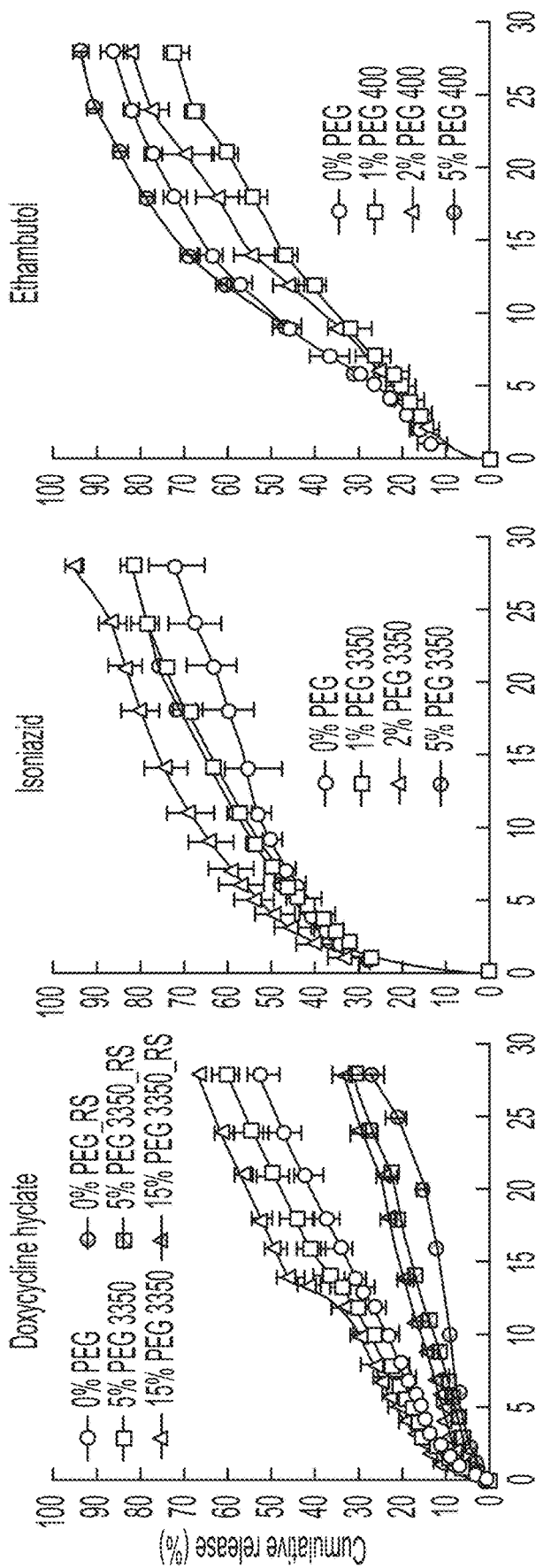
Figures 9E, 9F, 9G:
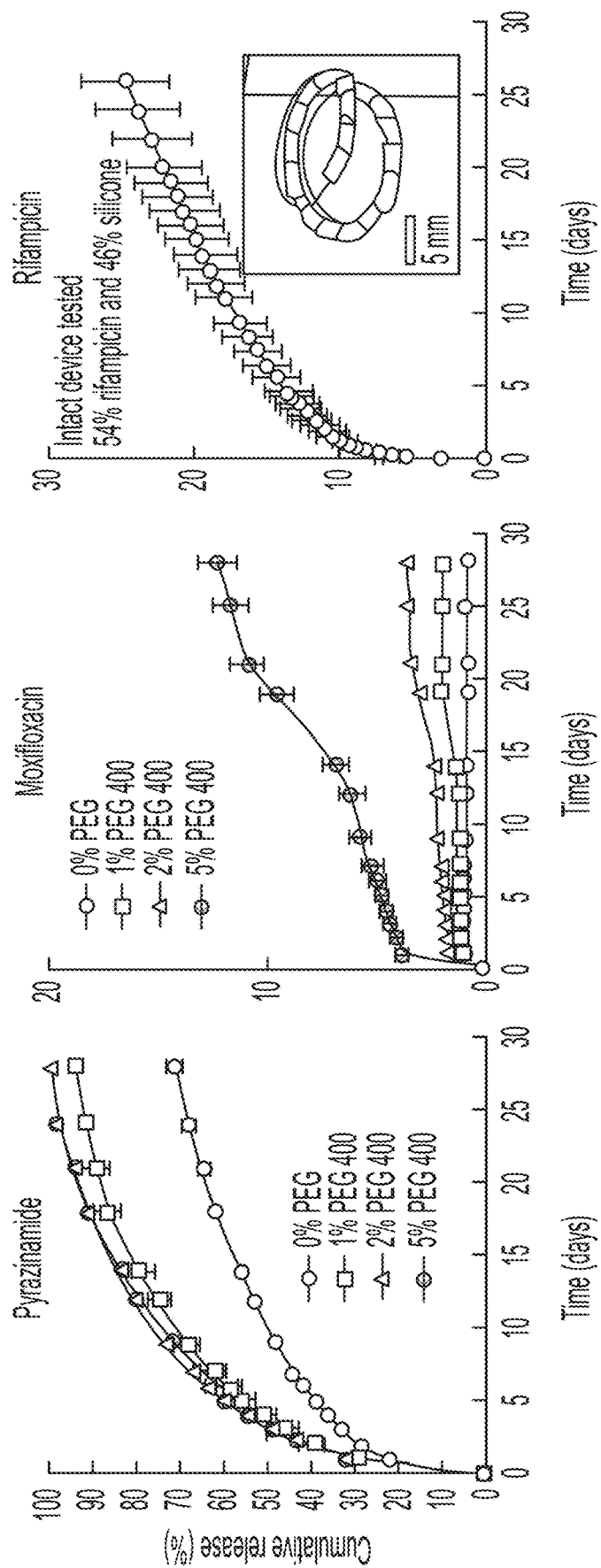
Figure 11A:
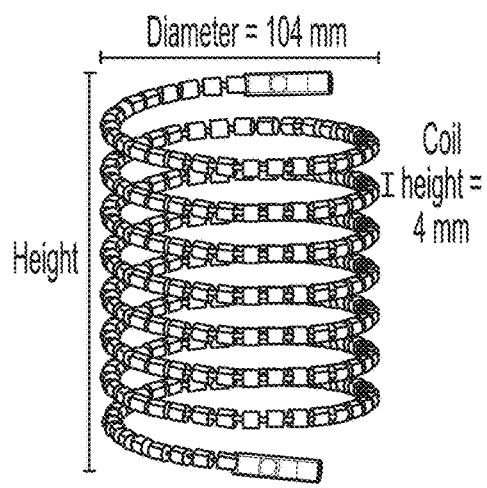
FIGS. 11A-11D shows physical parameters of the GRS as the drug weight increases, according to one set of embodiments. (11A) Diagram of the GRS and plot of height of device versus drug weight. The coil height is fixed at 4 mm due to the size of the measured drug pill height, and the diameter of the overall GRS is kept constant at 104 mm based on the size of the nitinol fixture (n=3). (11B) The calculated height of the GRS as a function of the drug weight, calculated by the number of pills that can fit on a single coil based on measurements of the pill height and diameter of the GRS. The number of coils is discrete; between a certain range of drug weight, the height of the device generally remains the same. (11C) The calculated overall end-to-end length of the uncoiled GRS according to the drug weight. (11D) The calculated total GRS weight according to the drug weight, incorporating the weight of the polymer matrix, nitinol wire, and ends of the device.
Figure 11B:
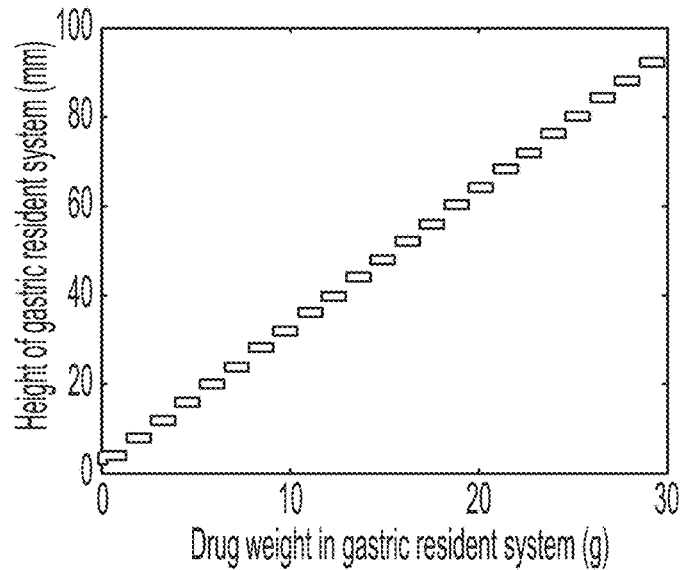
Figure 11C:
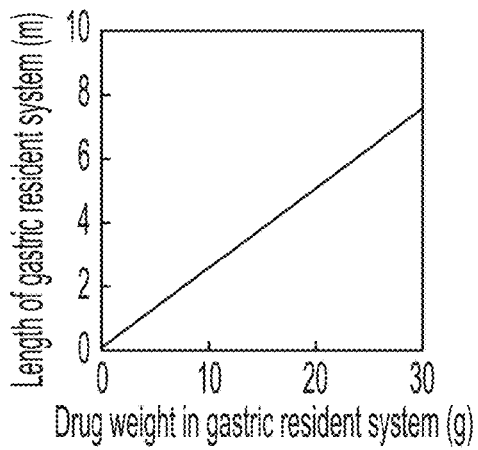
Figure 11D:
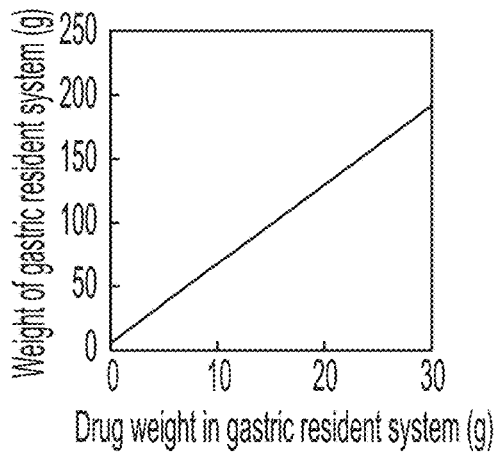
Figures 15A, 15B:
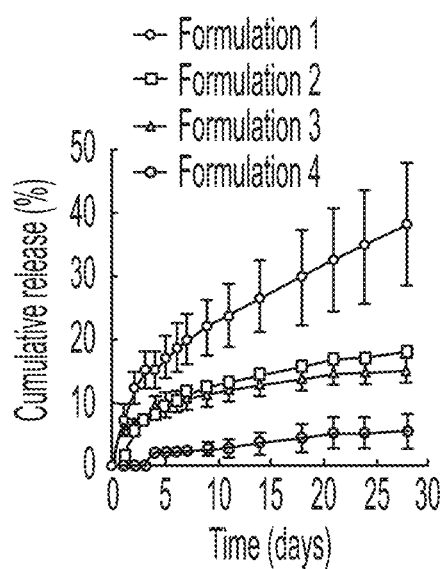
FIGS. 15A-15B shows in vivo formulations and their corresponding 4-week in vitro drug release profiles of doxycycline hyclate-silicone pills of the 10 g GRS, according to one set of embodiments. (15A) Table of in vivo formulations for the doxycycline hyclate-silicone pills of the 10 gram GRS assembled 1 gram of formulation 1, 2 grams of formulation 2, 3 grams of formulation 3, and 4 grams of formulation 4. Formulation 1 contained poly(ethylene glycol) (PEG), whereas the others did not. All drug pills were coated with either Eudragit RS 100 (formulations 1 and 2) or with poly(ε-caprolactone) (PCL) (formulations 3 and 4). (15B) In vitro release profiles of doxycycline hyclate from drug-silicone pills over 4 weeks in simulated gastric fluid.
Figure 16:
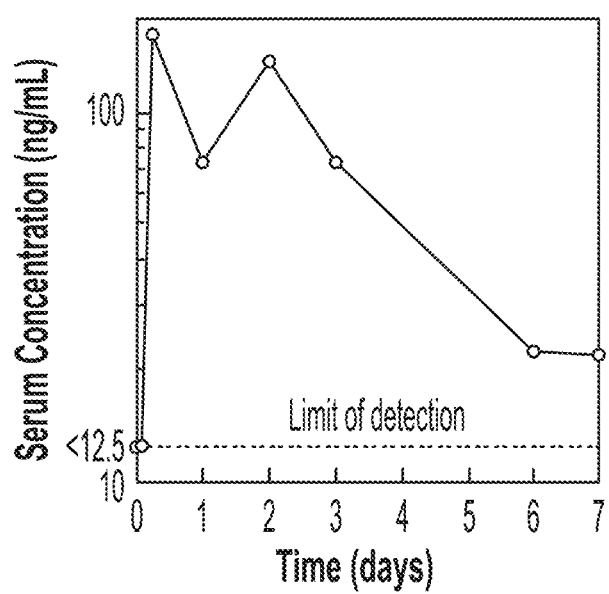
FIG. 16 shows in vivo release of rifampicin from the GRS in a swine model, according to one set of embodiments. A GRS with 2 grams of rifampicin formulated with 54% rifampicin and 46% silicone was administered to a swine model for 7 days, and the serum concentrations of rifampicin were recorded.
Figure 18A:
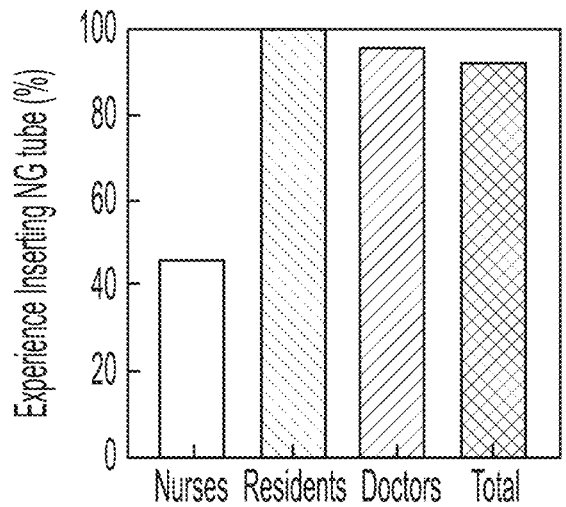
FIGS. 18A-18C shows field questionnaire results on NG tube deployment at TB clinics, according to one set of embodiments. (18A) Responses from all TB health care providers on their experience with inserting a NG tube previously. (18B) Responses from all TB health care providers on whether they agree with using a NG tube for deploying TB treatment. (18C) Responses from all TB health care providers on whether their hospital or clinic has the infrastructure to insert NG tubes in TB patients.
Figure 18B:
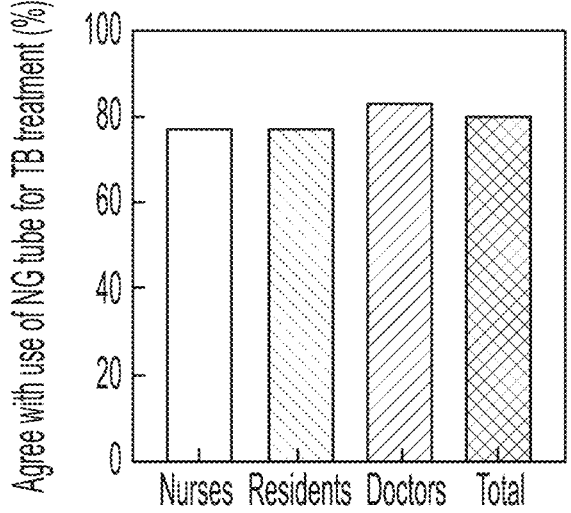
Figure 18C:
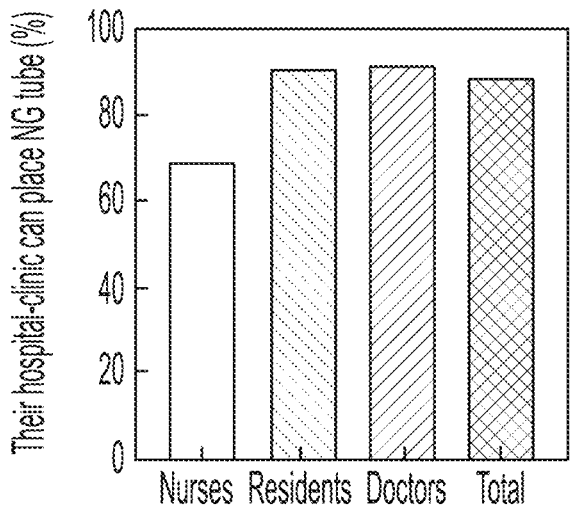

Drug-VPS pills were assmebled for multiple antibiotics used for TB treatment including doxycycline hyclate, isoniazid, ethambutol, pyrazinamide, moxifloxacin, and rifampicin. As demonstrated with doxycycline hyclate, the drug release rate from the VPS matrix in SGF may be tuned by varying the amount of a hydrophilic polymer, poly(ethylene glycol) (PEG), mixed within the VPS (FIG. 9B). The PEG domains acted as channels inside the hydrophobic VPS matrix that can dissolve and form pores for the doxycycline hyclate to release. Furthermore, formulations that were coated with Eudragit RS 100 showed a linear kinetic profile with limited burst release of doxycycline hyclate (FIG. 9B). The drug-VPS pills were also able to release isoniazid, ethambutol, pyrazinamide, moxifloxacin, and rifampicin in vitro, indicating that the VPS matrix is compatible with a wide variety of TB drugs (FIGS. 9C-G).
In Vivo Sustained Delivery of Antibiotic for 4 Weeks Having demonstrated controlled release with coated drug-matrix pills in vitro for 1 month, GRSs were loaded with 10 g of doxycycline hyclate as a model drug (FIG. 10A) and administered in swine. The GRS was assembled to contain 600 pills using four different formulations—two each with Eudragit RS 100 or PCL coatings—which released drug simultaneously (FIGS. 15A-15B). After 28 days of gastric residence in vivo, the GRS was safely retrieved (FIG. 10B). The serum concentration profile of a 100-mg single dose is shown in FIG. 10C. The drug was absorbed rapidly, and detectable concentrations were observed within 15 min. No drug was detectable after 3 days with the single-dose formulation. In contrast, drug was detectable for at least 28 days when doxycycline hyclate was dosed in the GRS. Rifampicin was also incorporated into the GRS and achieved detectable serum concentrations for a week in vivo (FIG. 16).
Preliminary End-User Assessment and Economic Impact of the GRS 111 TB health care providers and 300 patients were surveyed and learned that a long-term drug delivery device administered through an NG tube was acceptable and feasible in the field (FIGS. 17A-17F and 18A-18C). An established model was used to evaluate the potential impact of a GRS on patients with TB, with savings estimated at more than $8000 per patient.
General Discussion A GRS capable of multigram-level dosing of a TB antibiotic over the course of 4 weeks was developed. The GRS drug pills were generally compatible with all first-line TB antibiotics, and it was anticipated that further formulation development and large-scale manufacturing with an array of polymer matrices and coatings will optimize a linear drug release profile in the gastric cavity to reduce variability in serum concentrations and match drug release kinetics across drugs. These macrodevices showed no evidence of GI obstruction or injury during gastric residence and retrieval, as supported by radiographic, endoscopic, and histopathologic evaluation in a swine model.

Adherence to TB treatment is generally challenging because of the long and frequent dosing regimen, and additional patient-centered interventions may be necessary to supplement directly observed therapy short course (DOTS) in resource-constrained environments. Technologies such as the GRS described here can improve the effectiveness of DOTS by ensuring that patients receive their medication over the course of extended periods of time, thereby reducing the frequency of clinic visits. Less frequent dosing visits would reduce the potential impact on daily life, specifically on productivity of individuals receiving treatment for TB. The ability of the GRS to contain and serve as a multigram drug depot in the gastric cavity supports further development of prolonged drug depots on the order of weeks and even months, which could mitigate the effects of poor adherence.

To establish a route for translation, it was anticipated that the full development of these devices will include preclinical evaluation in an additional animal model such as the dog. Optimizing drug release kinetics is a critical next step, such that serum concentrations of the drug remain within the therapeutic window and do not generally increase the likelihood of drug resistance. Different diet conditions may be tested to understand the effect on pharmacokinetic parameters across a broad spectrum of drugs.

In addition, the importance of amplifying training of health care workers to deploy NG tubes safely was recognized, so that the GRS can be implemented alongside DOTS interventions in the field where trained personnel are generally present. Because patients will be conscious during the NG tube procedure, they will be able to speak to a health care worker to ensure correct placement of the tube.

To begin addressing the acceptability and feasibility of the NG tube approach, a preliminary field questionnaire of 300 patients with TB and 111 TB health care workers in TB clinics. Survey results indicated that more than 90% of health care personnel have experience deploying NG tubes, and patients prefer the use of an NG tube for deployment of a month-long TB treatment as opposed to swallowing many capsules or drinking liters of water-drug mixture as potential alternative modes of generating large drug depots. It was further demonstrated that the potential impact of the implementation of our GRS to improve adherence in terms of lives saved and economic savings for patients suffering from TB.

Macrodevices consisting of multigram drug depots could have an impact across a range of diseases in addition to TB and could be coupled to other procedures such as endoscopy. For broad implementation, a range of chemical therapeutics may be incorporated into the modular pill design of the GRS. Formulations may be optimized to ensure high drug loading efficiencies and controlled release profiles for efficacious treatment and controlled drug release. The GRS has potential as a platform technology for improving medication adherence and thereby also improve outcomes for patients suffering from a myriad of diseases.

Materials and Methods

Study Design

Devices for month-long drug delivery in the gastric cavity were designed, fabricated, and tested. In some embodiments, the GRS contains a series of drug pills loaded onto a nitinol shape memory alloy wire. The device may form a coil shape after reaching the stomach. A retrieval device compatible with nasogastric administration may use a sensor and magnet to attach to a magnet on the GRS. Radiographic, endoscopic, and histopathologic evaluation were conducted.

End-user acceptability and feasibility of NG tube placement was assessed through a questionnaire of 111 TB health care providers and 300 patients with TB at DOTS clinics. Sample sizes were determined on the basis of a conservative method with a 90% confidence interval and 8% margin of error for the health care providers and 90% confidence interval and 5% margin of error for the patients. All health care providers who filled out more than 90% of the questionnaire were included in the analysis. All 300 patients who provided consent for the study were included in the analysis. An economic model was applied to quantify the impact of the GRS.

Manufacturing of the Gastric Resident System (GRS)

The assembled GRS consisted of a superelastic nitinol wire as the retention frame upon which drug pills are strung with a retainer and tubing at the ends of the device. Nitinol wire, with diameter of 0.59 mm and phase transformation at 37° C., was wrapped around a custom fixture to create a helical shape and secured in place using steel screws. The nitinol-fixture assembly was placed in a furnace at 500° C. for 15 minutes and then quenched in water at room temperature for 20 minutes. The nitinol was unwrapped from the fixture, ready for pills to be added.

Doxycycline hyclate was purchased from MedChem Express LLC. Isoniazid was purchased from Sigma-Aldrich Corporation, and moxifloxacin was purchased from ArkPharm, Inc. Rifampicin, ethambutol, and pyrazinamide were purchased from Hangzhou Hysen Pharma Co. Ltd. Drug pills were made using the following protocol: The drug was first added to the vinylpolysiloxane (VPS) base (Zhermack Elite Double 22) and mixed at 3200 rpm for 30 seconds using a SpeedMixer DAC 150.1 FVX-K (FlackTek Inc.). To prevent drug loss, it was ensured that all the drug was mixed into the matrix before proceeding. After 2 minutes of cooling, poly(ethylene glycol) (PEG) molecular weight 3500 (Sigma-Aldrich Corporation) or molecular weight 400 (Sigma-Aldrich Corporation) was added and mixed into the drug-VPS base matrix using the SpeedMixer at 2700 rpm for 30 seconds. After 2 minutes of cooling, the VPS catalyst (Zhermack Elite Double 22) was added and mixed using the SpeedMixer at 1750 rpm for 30 seconds. Drug loading percentages were determined relative to the final cured silicone mixture weight: doxycycline hyclate (32%), isoniazid (32%), ethambutol (25%), pyrazinamide (30%), moxifloxacin (20%), and rifampicin (54%). The viscous uniform blend was poured into a disposable polystyrene Petri dish (VWR), and individual pills were extracted using a 4 mm Miltex disposable biopsy punch (Integra). A 0.5 mm biopsy punch (Electron Microscopy Sciences) was used to core out a hole in the center of the drug-VPS pill to allow the nitinol wire to pass through.

The pills were spray-coated in a DKE stainless steel pan (ERWEKA GmbH) with a 9.5 L capacity attached to an AR 403 drive unit (ERWEKA GmbH). The Eudragit RS 100 (Evonik Corporation) solution was prepared as recommended by Evonik (60). Briefly, the Eudragit RS 100 pellets were dissolved in 50% of a diluent mixture, composed of 342.90 grams of acetone (Sigma-Aldrich Corporation), 514.20 grams of isopropanol (Sigma-Aldrich Corporation), and 42.90 grams of water. In a separate beaker, an excipient mixture of talc (<10 um particle size from Sigma-Aldrich Corporation), triethyl citrate (Sigma-Aldrich Corporation), and red dextrose food dye (CK Products) was homogenized into the remaining 50% of the diluent mixture for 15 minutes. The excipient mixture was then poured into the beaker containing the Eudragit solution and stirred. Lastly, the spray suspension was passed through a 500 μm sieve (McMaster-Carr). To prepare a poly(ε-caprolactone) (PCL) spray solution, PCL molecular weight 45,000 (Sigma-Aldrich Corporation) was added to acetone at 5% weight per volume. The solution was then placed on a hot plate with a stir bar at 50° C. and 200 rpm. The PCL pellets started to fully dissolve and form a homogenous solution after one hour. The spray gun used was a 0.8 mm nozzle, handheld Master E91 airbrush (TCP Global) attached to beakers in the kit with a spray volume of 18 mL and held at a 90° angle to the rotating pan with a 7 cm distance from its outer diameter. The coating pan was tilted at a 45-degree angle for all the formulations and rotated at 70 rpm for the Eudragit RS 100 solution and at 300 rpm for the PCL solution. A heat gun (Uline) was placed directly underneath the coating pan and set to 50° C. to induce film formation on the pills sprayed with Eudragit RS 100. The Eudragit RS 100 sprayed pills were dried for 2 hours after spraying in a circulating air oven set at 40° C. The typical batch size for spraying was 100 pills. It took 120 minutes to spray pills with 300 mL of Eudragit RS 100, and it took 100 minutes to spray pills with PCL.

The nitinol wire was inserted into the 0.5 mm hole of the coated drug-VPS pills, and after the desired loading was achieved, each end of the nitinol wire was crimped using a pair of pliers. PCL molecular weight 37,000 (Sigma-Aldrich Corporation) pellets were then pressed into two 3-inch (76.2 mm) long pieces of Tygon tubing (Inner Diameter×Outer Diameter: 4.76×6.35 mm), which was obtained from McMaster-Carr. The end of each tube was then filled with Med3-4213 silicone adhesive (NuSil), followed by a 6.35 mm stainless steel ball bearing. Once completely packed with the pellets, the tubes were heated at 100° C. to melt the PCL using a heat gun. Each crimped end of the nitinol was then slowly inserted into the molten PCL and set into place as the PCL cooled at room temperature to solidify around the nitinol wire. More silicone adhesive was used to seal the free ends of the tubes at both ends of the device.

In Vivo Evaluation of the Immediate Release and Gastric Resident System (GRS)

To assess the oral pharmacokinetics of immediate release formulations and gastric retentive drug delivery devices, they were administered to a large animal model (30-75 kg Yorkshire pigs). This model was chosen because its gastric anatomy is similar to that of humans and is widely used in evaluating devices in the GI tract. Animals were fed daily in the morning and in the evening with a diet consisting of pellets (Laboratory mini-pig grower diet, 5081), in addition to a midday snack consisting of various fruits and vegetables. The pellets consisted of ground oats, alfalfa meal, wheat middlings, soybean meal, dried beet pulp, salts, and other micronutrients.

The immediate release formulation was prepared by weighing and filling 100 mg of doxycycline hyclate in a "00" gelatin capsule (Purecaps USA) 15 minutes prior to dosing. Prior to dosing, the pigs were sedated with Telazol® (5 mg/kg IM), xylazine (2 mg/kg IM), and atropine (0.04 mg/kg IM), intubated, and maintained with isoflurane (1 to 3% inhaled).

Immediate release and GRS formulations were deployed in the stomach via an endoscopic guided overtube (Inner Diameter×Outer Diameter: 16.7×19.5 mm) from US Endoscopy. The overtube was removed once the devices were administered. For evaluation of the safety and residence time of the gastric retentive drug delivery devices, the animals were clinically assessed twice a day for evidence of GI obstruction including inappetence, abdominal distension, lack of stool, and vomiting. Additionally, the animals were evaluated radiographically every day 3-4 days for evidence of GI obstruction and/or perforation. Tissue samples were collected before and after the device was placed in the stomach for histopathological analysis, and macroscopic images were taken once the device was retrieved to study any possible mucosal damage. Blood samples were obtained from an external mammary vein on the ventral surface of the pig at indicated time points. Serum samples were separated from blood by centrifugation (3220 rpm, 10 min at 4° C.) and were stored at −80° C. for further analysis.

Manufacturing and Evaluation of the Retrieval Device

The retrieval device was constructed using three 4.76 mm diameter×4.76 mm length cylindrical neodymium magnets with pull force of 10.14 Newtons (K&J Magnetics, Inc.) and an Allegro A1324 linear Hall effect sensor (Modern Device), all housed in a 1-meter long Tygon tube (Inner Diameter× Outer Diameter: 4.76×6.35 mm). The sensor and magnets were placed on one end of the Tygon tube, with the sensing face of the sensor bent at a 45-degree angle relative to the magnets. Each pin of the sensor was soldered to a 26-gauge, solid electrical wire (Adafruit Industries LLC) and covered in heat shrink tubing to avoid shorting the sensor. A thin layer of Med3-4213 silicone adhesive was applied at the tip of the outermost magnet to give the magnets a slight downward offset from the top surface of the tubing and keep the magnets of the retrieval device slightly separated from the magnet of the drug delivery device upon connection. An Arduino Pro Mini 328 (SparkFun Electronics) received the output of the Hall effect sensor and sent a text output to a serial-enabled liquid crystal display (SparkFun Electronics). When the magnets of the retrieval device connected with the magnet of the GRS, defined by a Hall effect sensor output that exceeded a given voltage threshold for at least one minute, the liquid crystal display showed the message "The magnets are connected." A 3.7 V lithium ion battery (Spark-Fun Electronics) powered the microcontroller circuit.

The stability of the Allegro A1324 Hall effect sensor was tested in air first and then after immersion in simulated gastric fluid, USP without pepsin (pH~1.2; henceforth referred to as SGF). The sensing area of the insulated sensors was covered with two-part epoxy (Devcon). The insulated sensor was placed in 4 mL of SGF for 90 minutes and then removed. After this period, the sensors and a 4.76 mm×4.76 mm cylindrical neodymium magnet were fixed in place, with 10 mm separating the sensing face of the sensor and the south pole of the magnet. The sensor voltage output was read and recorded via the Arduino integrated development environment serial monitor to compare with the voltage read prior to immersion in SGF.

For in vivo evaluation of the retrieval device interaction with the GRS, the animals were sedated, intubated, and maintained with isoflurane as described above. The GRS was first deployed in the stomach via an endoscopic guided overtube, and radiographs confirmed placement of the device in the gastric cavity. The retrieval device was then inserted into the overtube without endoscopic guidance to demonstrate the ability of the Hall effect sensor on the retrieval device to detect the magnet on the GRS. Radiographs were captured of the retrieval device as it entered the gastric cavity, contacted the GRS as indicated on the liquid crystal display board, and successfully retrieved the GRS.

In Vitro Stomach Model

A three-dimensional (3D) model mimicking the human stomach was designed in SolidWorks (Dassault Systemes) and created to analyze feasibility of the delivery and retrieval of the GRS. The 3D part was split into two halves and then printed on a Stratasys Objet30 3D printer. Polyethylene terephthalate (PETG) sheets from McMaster-Carr with 3.175 mm thickness were formed around the stomach halves using a heat gun. A band saw (Home Depot) was used to trim the excess material away, leaving the PETG half stomach with a 25.4 mm border. The outline of the stomach shape designed on SolidWorks was used to generate a custom gasket for sealing the two halves of the in vitro model together. Two of these gaskets were laser cut out of 1.59 mm thick silicon rubber sheets (McMaster-Carr) using a Universal Laser Systems VLS6.60 and then glued onto each of the stomach halves with cyanoacrylate (Krazy Glue). About every 5 cm, clearance holes for M6 bolts (McMaster-Carr) were drilled around the perimeter of both halves.

The nasal passage, pharynx, and esophagus were modelled out of a 0.6-meter long PETG tubing (Inner Diameter× Outer Diameter: 9.525×12.7 mm) from McMaster-Carr. The tubing was bent with a heat gun to form a 90-degree turn. To interface the tubing into one stomach half, a custom adapter was printed using a Formlabs Form 2 3D printer. The bottom end of the tubing was heated with a heat gun and press fit into the adapter. The upper section of the stomach half was also heated using a heat gun and fitted with the other side of the adapter. The two halves of the stomach were aligned, and 13 M6 bolts were used to secure the halves together and make the stomach model water tight.

Drug Release In Vitro

Individual pills made of drug-VPS for doxycycline hyclate, isoniazid, ethambutol, pyrazinamide, moxifloxacin were used to evaluate long-term release kinetics in SGF. Pill formulations were incubated in a New Brunswick Innova 44 shaking incubator (Eppendorf) at 37° C. and 200 rpm in 50 mL of SGF for up to 28 days, with solution exchanges at specified time intervals. Drug concentrations were then analyzed using a High-Performance Liquid Chromatography (HPLC). Because of the lack of a validated HPLC method for evaluating isoniazid in SGF, water was used to study differences between isoniazid formulations. Three intact rifampicin devices were fabricated by loading 2 grams of drug into VPS pills. The devices were incubated in 500 mL of nanopure water for up to 26 days in a shaking incubator at 37° C. and 200 rpm, with media exchange at specified time intervals. Water was used as a solvent for the drug release study because rifampicin generally rapidly degrades in acid. The drug concentrations samples were then measured on an Infinite M200Pro (Tecan) reader (absorbance, 475 nm).

High-Performance Liquid Chromatography

An Agilent 1260 Infinity II HPLC system (Agilent Technologies, Inc.) equipped with a Model 1260 quaternary pump, Model 1260 High Performance autosampler, Model 1260 thermostat, Model 1260 Infinity Thermostatted Column Compartment control module, and Model 1260 diode array detector was utilized. Data processing and analysis was performed using OpenLab CDS ChemStation (Agilent Technologies, Inc.). All solvents used were purchased from Sigma-Aldrich Corporation. For doxycycline hyclate, chromatographic isocratic separation was carried out on an Agilent 4.6×50 mm AdvanceBio RP-mAb SB-C8 analytical column with 3.5 µm particles, maintained at 55° C. The optimized mobile phase consisted of 20 mM dipotassium phosphate buffer and acetonitrile (pH 6 adjusted with triethylamine) [60:40 (v/v)] at a flow rate of 0.85 mL/min over a 4 min run time. The injection volume was 5 µl, and the selected ultraviolet (UV) detection wavelength was 293 nm.

For isoniazid and pyrazinamide, chromatographic isocratic separations were carried out on an Agilent 4.6×150 mm ZORBAX Eclipse Plus C-18 analytical column with 5 µm particles, maintained at 30° C. The optimized mobile phase consisted of 10 mM sodium dibasic phosphate buffer and acetonitrile (pH 6.75 adjusted with phosphoric acid) [95:5 (v/v)] at a flow rate of 1.00 mL/min over a 6 min run time. The injection volume for both drugs was 20 µl, and both drugs were analyzed using a UV detection wavelength of 238 nm. For moxifloxacin, chromatographic separation was carried out on an Agilent 4.6×50 mm Poroshell 120 EC-C18 analytical column with 2.7 µm particles, maintained at 50° C. The optimized gradient consisted of nano-pure water and acetonitrile starting at [95:5 (v/v)] at 0 minutes then ramping to [50:50 (v/v)] at 2.5 minutes and descending to [95:5 (v/v)] by 5 minutes. A constant flow rate was maintained at 1.00 mL/min, and a post-run of 1 minute was utilized. The injection volume was 5 µl, and the UV detection wavelength of 293 nm was selected.

For ethambutol, chromatographic separation was achieved using a method described previously. A Waters 3.9×300 mm µBondapak C18 analytical column with 10 µm particles, maintained at 35° C., was utilized in an isocratic elution method. The optimized mobile phase consisted of buffered nano-pure water (1.0 mM Cu(II)SO4, 4 g sodium 1-heptanesulfonate, titrated to pH 4.50 with 10 mM HCl) and tetrahydrofuran [75:25 (v/v)]. A constant flow rate was maintained at 1.50 mL/min for 15 minutes, and a post-run of 1 minute was utilized. The injection volume was 20 µl, and the ultraviolet (UV) detection wavelength of 260 nm was selected.

Liquid Chromatography-Tandem Mass Spectrometry

Drug concentrations in serum from in vivo experiments were analyzed using Ultra-Performance Liquid Chromatography-Tandem Mass Spectrometry (UPLC-MS/MS). Analysis was performed with a Waters ACQUITY UPLC-I-Class System aligned with a Waters Xevo-TQ-S mass spectrometer (Waters Corporation). Liquid chromatographic separation was performed on an Acquity UPLC Charged Surface Hybrid C18 (50 mm×2.1 mm, 1.7 µm particle size) column at 50° C. The mobile phase consisted of aqueous 0.1% formic acid, 10 mM ammonium formate solution (Mobile Phase A) and acetonitrile:10 mM ammonium formate, 0.1% formic acid solution (95:5 v/v) (Mobile Phase B). The mobile phase had a continuous flow rate of 0.6 mL/min using a time and solvent gradient composition. For the analysis of doxycycline hyclate, the initial composition (100% Mobile Phase A) was held for 1 minute, following which the composition was changed linearly to 50% Mobile Phase A over the next 0.25 minutes. At 1.5 minutes, the composition was 20% Mobile Phase A. At 2.5 minutes, the composition was 0% Mobile Phase A and 100% Mobile Phase B, which was held constant until 3 minutes. The composition returned to 100% Mobile Phase A at 3.25 minutes and was held at this composition until completion of the run, ending at 4 minutes, where it remained for column equilibration. The total run time was 4 minutes. For the analysis of rifampicin, the initial composition (95% Mobile Phase A) was held for 0.5 minutes, following which the composition was changed linearly to 15% Mobile Phase A over the next 1.25 minutes. At 1.76 minutes, the composition was 0% Mobile Phase A and 100% Mobile Phase B, which was held constant until 3.25 minutes. The composition returned to 95% Mobile Phase A at 3.50 minutes and was held at this composition until completion of the run, ending at 4.50 minutes, where it remained for column equilibration. The total run time was 4.5 minutes.

For both the analysis of doxycycline hyclate and rifampicin, the sample injection volume was 2.5 µL. The mass spectrometer was operated in the multiple reaction monitoring mode. The mass to charge transitions (m/z) used to quantitate doxycycline hyclate, demeclocycline hydrochloride, rifampicin, and rifapentine were 445.19>154.1, 465.13>154.09, 823.5>151.17, and 877.55>151.18, respectively. Sample introduction and ionization was by electrospray ionization (ESI) in the positive ionization mode. Waters MassLynx 4.1 software was used for data acquisition and analysis.

Stock solutions of doxycycline hyclate, rifampicin, internal standards (IS) demeclocycline hydrochloride and rifapentine were prepared in methanol at a concentration of 500 µg/mL. A twelve-point calibration curve was prepared in analyte-free, blank serum ranging from 1-5000 ng/mL. 100 µL of each serum sample was spiked with 200 µL of 250 ng/mL IS in acetonitrile to elicit protein precipitation. Samples were vortexed and sonicated for 10 minutes and centrifuged for 10 minutes at 13000 rpm. 200 µL of supernatant was pipetted into a 96-well plate containing 200 µL of nanopure water. Finally, 2.5 µL was injected onto the UPLC-ESI-MS system for analysis.

Questionnaire Study

The four approaches for improving adherence were chosen by incorporating both behavioral and technological interventions. Three routes of administration are generally compatible with multigram dosing and deployment through the esophagus: 1) placing a nasogastric (NG) tube to deploy a GRS, 2) swallowing many capsules, and 3) drinking water-drug mixture (inspired by the recent developments in gastric resident hydrogels). These options were presented to health care providers and patients with approximate volumes of the drug necessary. Emphasis on the need for these routes to be administered in a TB clinic was placed to maximize the efficacy of the directly observed treatment short course (DOTS) strategy.

Example 6

Figure 19A:
FIG. 19A is a photograph of an exemplary article in a straight (first) configuration, according to one set of embodiments.
Figure 19B:
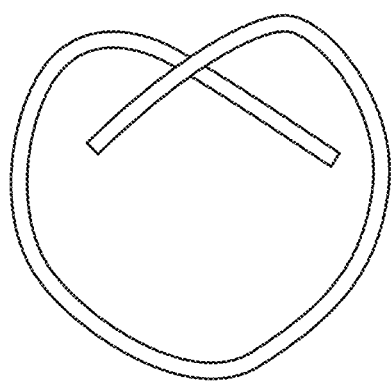
FIG. 19B is a photograph of an exemplary article in a second configuration, according to one set of embodiments.

J-hook shape that can first be stretched into a straight configuration during deployment to the stomach (FIG. 19A). Once the force is removed from the device, it relaxes into the pre-determined shape set by a retention frame, such as nitinol "superelastic" wire (FIG. 19B). Outside the wire is FDA-approved flexible tubing that is used for housing the API. The length of the device must be at least 28.66 cm to hold 10 grams of API. Multiple apertures can be drilled in the tubing to allow for drug diffusion. The retention frame must be thick enough to enable the flexible tubing to comply and form the pre-determined shape in vivo. The ends of the device are sealed with a magnetic element and silicone adhesive. The magnetic element facilitates retrieval back through the nasogastric or endoscopic tube with retrieval devices, which we have written about in another disclosure.

Figure 19C:
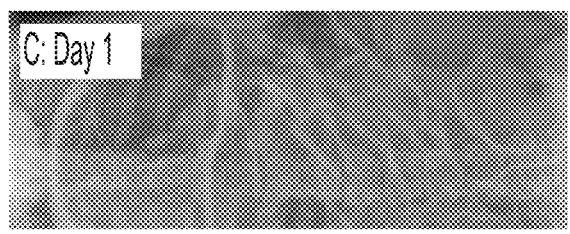
FIG. 19C is an x-ray of an exemplary article in the stomach of a subject, according to one set of embodiments.
Figure 19D:
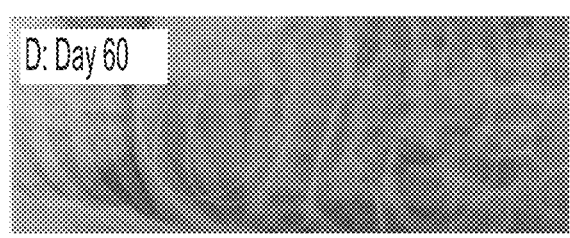
FIG. 19D is an x-ray of an exemplary article in the stomach of a subject, according to one set of embodiments.

After deployment in a large animal model, serial chest/abdominal X rays were obtained demonstrating gastric retention. FIG. 19C shows the device in the stomach of a large animal on the first day of deployment. FIG. 19D shows the same device in the stomach of a large animal 60 days after deployment, thus demonstrating gastric retention.

Example 7

Figure 20A:
FIG. 20A is a photograph of an exemplary article in a straight (first) configuration, according to one set of embodiments.
Figure 20B:
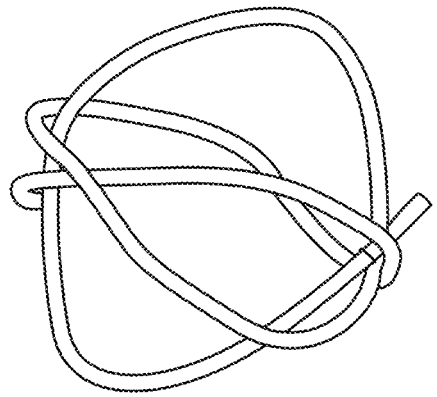
FIG. 20B is a photograph of an exemplary article in a second configuration, according to one set of embodiments.

Sphere shape that can first be stretched into a straight configuration during deployment to the stomach (FIG. 20A). Once the force is removed from the device, it relaxes into the pre-determined shape set by a retention frame, such as nitinol "superelastic" wire (FIG. 20B). Outside the wire is FDA-approved tubing that is used for housing the API. The length of the device must be at least 28.66 cm to hold 10 grams of API. Multiple apertures can be drilled in the tubing to allow for drug diffusion. The retention frame must be thick enough to enable the flexible tubing to comply and form the pre-determined shape in vivo. The ends of the device are sealed with a magnetic element and silicone adhesive. The magnetic element facilitates retrieval back through the nasogastric or endoscopic tube with retrieval devices, which we have written about in another disclosure.

Example 8

Figure 21A:
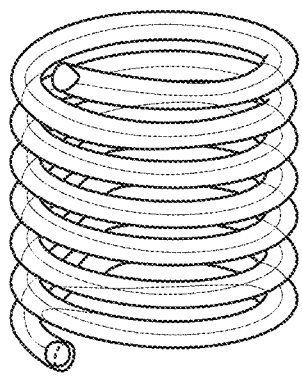
FIG. 21A is a schematic illustration of an exemplary article in a particular configuration, according to one set of embodiments.

In another implementation shown in FIG. 21A, a series of circles can be arranged in a three-dimensional fashion to make a cylindrical shaped device. Outside the wire is FDA-approved flexible tubing that is used for housing the API. The length of the device must be at least 28.66 cm to hold 10 grams of API. Multiple apertures can be drilled in the tubing to allow for drug diffusion. The retention frame must be thick enough to enable the flexible tubing to comply and form the pre-determined shape in vivo. The ends of the device are sealed with a magnetic element and silicone adhesive. The magnetic element facilitates retrieval back through the nasogastric or endoscopic tube with retrieval devices, which we have written about in another disclosure.

Figure 21B:
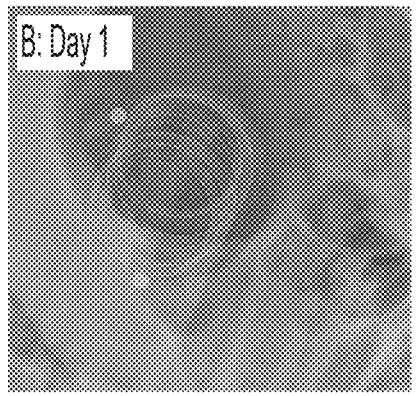
FIG. 21B is an x-ray of an exemplary article in the stomach of a subject, according to one set of embodiments.
Figure 21C:
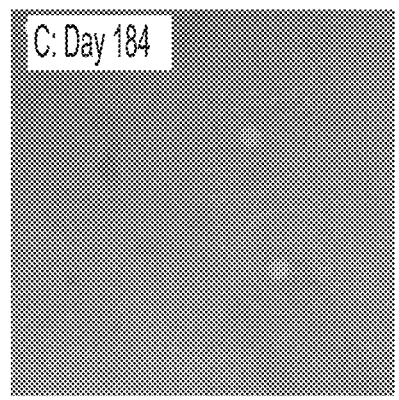
FIG. 21C is an x-ray of an exemplary article in the stomach of a subject, according to one set of embodiments.

After deployment in a large animal model, serial chest/abdominal X rays were obtained demonstrating gastric retention. FIG. 21B shows the device in the stomach of a large animal on the first day of deployment. FIG. 21C shows the same device in the stomach of a large animal 184 days after deployment, thus demonstrating gastric retention.

Example 9

Figure 22:
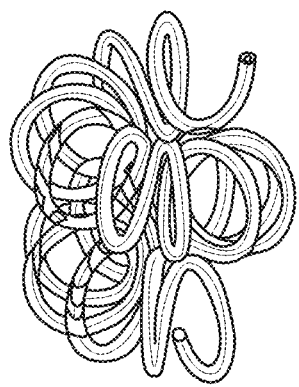
FIG. 22 is a schematic illustration of an exemplary article in a particular configuration, according to one set of embodiments.

FIG. 22 shows another structure that assembles into a toroid-inspired shape, Outside the wire is FDA-approved flexible tubing that is used for housing the API. The length of the device must be at least 28.66 cm to hold 10 grams of API. Multiple apertures can be drilled in the tubing to allow for drug diffusion. The retention frame must be thick enough to enable the flexible tubing to comply and form the pre-determined shape in vivo. The ends of the device are sealed with a magnetic element and silicone adhesive. The magnetic element facilitates retrieval back through the nasogastric or endoscopic tube with retrieval devices, which we have written about in another disclosure.

Example 10

Figure 23:
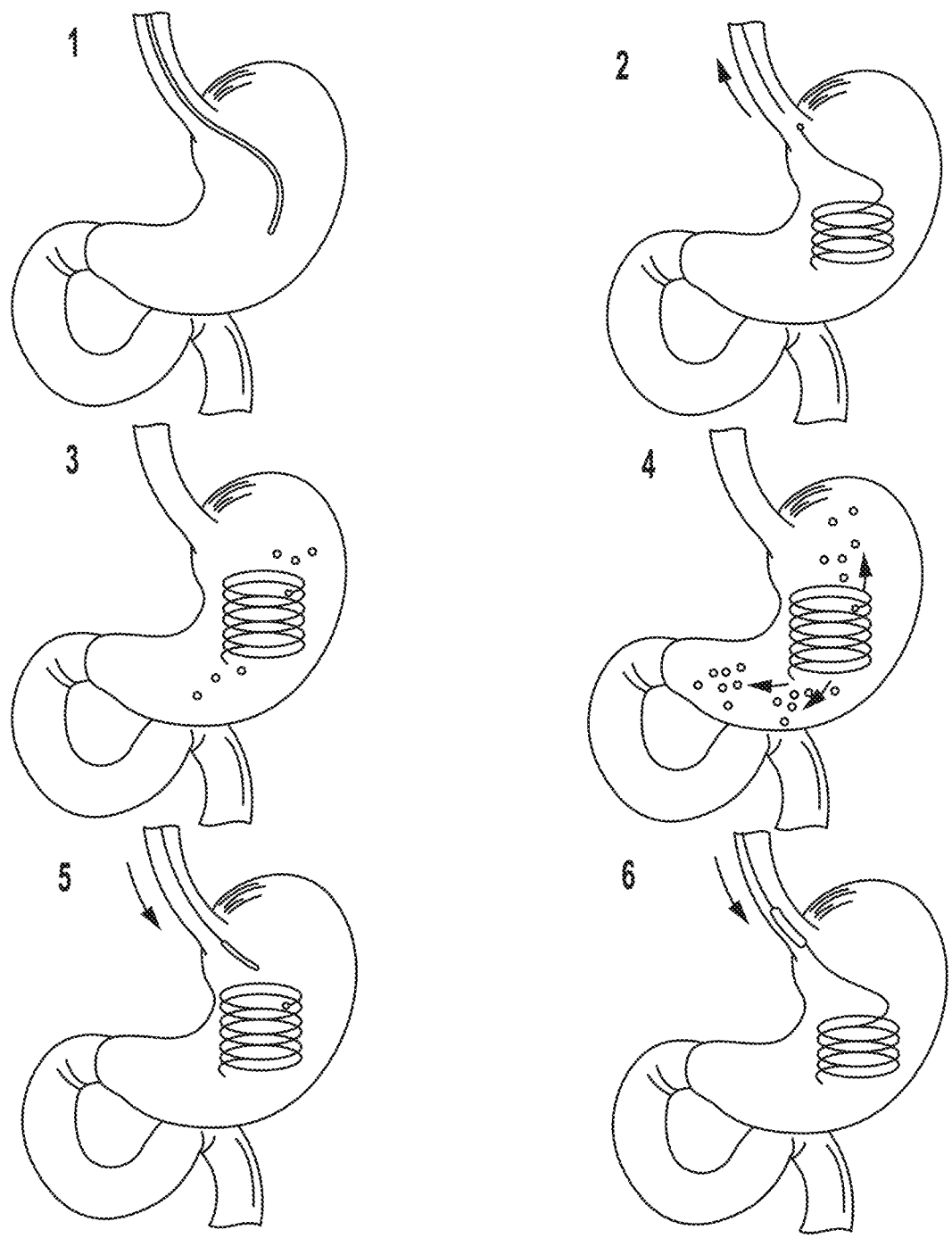
FIG. 23 is a schematic illustration of administration of an exemplary article, according to one set of embodiments.

FIG. 23 shows an exemplary route of administration of articles described herein to a location internal to a subject. For example, the article may be (1) administered via a transesophageal route having a first shape/configuration where, upon removal of an elastic wire, it (2) obtains a second shape/configuration. (3-4) A therapeutic agent may be released from the article as it resides in the location internal to the subject. At a desired time (5-6) the article may be retrieved via transesophageal retrieval.

Example 11

The retrieval system was constructed using a 3/16 inch cylindrical neodynium magnet and a Allegro A1324 linear hall effect sensor all housed in Tygon tubing with outer diameter ¼ inch and inner diameter of 3/16 inch (FIG. 24A). The sensor has 3 pins, and each pin is soldered to a 26 gauge, solid electrical wire. The electrical wires are all covered with 0.045 inch inner diameter miniature heat shrink tubing to avoid shorting the sensor. A 5 Volt battery was used to power the sensor. An Arduino Uno aws used to provide meaningful output to the user on when the magnet of the retrieval system is connected with the magnet of the gastric resident system, so the LCD could display "The magnets are connected."

The retrieval system successfully retrieved gastric resident systems 3 times. A cylindrical gastric resident system was administered to a large animal (FIG. 24B). It had 2 magnets, one on each side. The retrieval system was then inserted through an esophageal overtube (FIG. 24C), it made contact with the magnet on the cylindrical gastric resident (FIG. 24D) and then the LCD display indicated the magnets are connected, and the gastric resident system was successfully retrieved through the overtube by the retrieval system (FIG. 1E).

Example 12

Figures 25A, 25B, 25C, 25D, 25E:
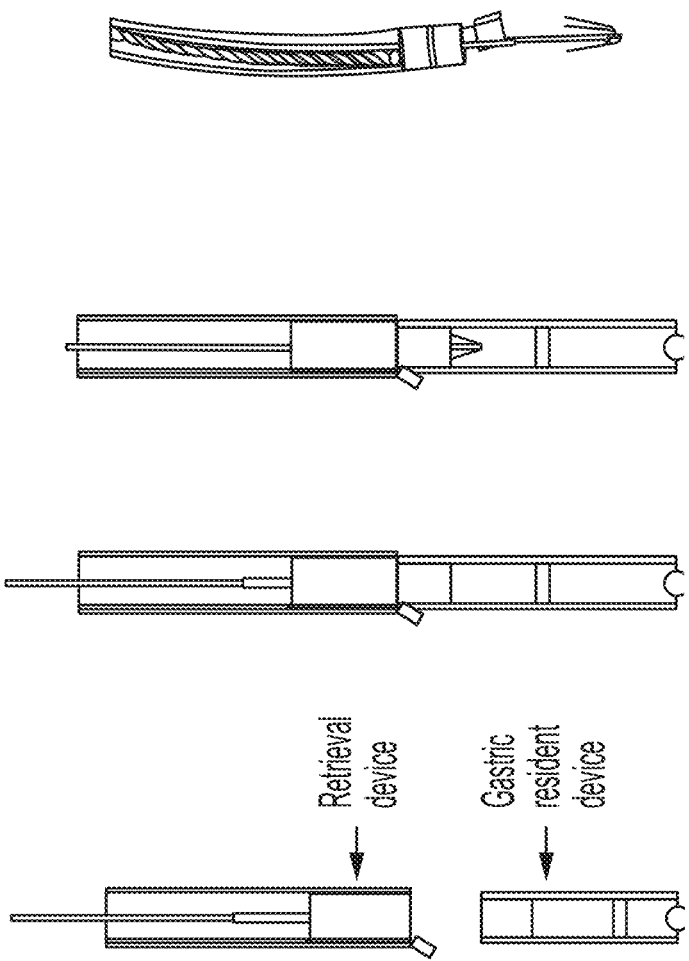
FIGS. 25A-25C are schematic illustrations of an exemplary retrieval system configured to retrieve a gastric residence system, according to one set of embodiments.
FIG. 25D is a photograph of an exemplary retrieval system, according to one set of embodiments.
FIG. 25E is an x-ray image of an exemplary retrieval system (FIG. 25D) used to a retrieve a gastric residence system from the stomach of a subject, according to one set of embodiments.

In another design, the retrieval system incorporated a fishing hook-type design. It used barbs made of 0.01 inch diameter nitinol wire to lift up a gastric resident system (FIGS. 25A-25C). The retrieval system has two ring neodymium magnets with ¼ inch outer diameter and 1/16 inch inner diameter and a Allegro A1324 linear hall effect sensor all housed in Tygon tubing with outer diameter ¼ inch and inner diameter of 3/16 inch (FIG. 25D). The barbs are only extended out of the retrieval system once the retrieval system has made contact with the drug delivery system. FIG. 25D shows the retrieval system with the barbs extended out. FIG. 25E shows successful contact and retrieval of the retrieval system with barbs.

The barbs are made of 0.01 inch diameter nitinol that can cooked on a fixture at 500 degrees Fahrenheit for 20 minutes and then quenches in cold water. The fixture has pins and bolts positioned in a manner that allows the nitinol to be cooked at various bend angles. The angle of the barbs (FIG. 26A) may be chosen depending on the maximum impulse for lifting a gastric resident system. Instron testing was done to determine the impulse for barb angles ranging from 13.5 to 27.7 degrees, with 20.3 degrees being the optimal barb angle (FIG. 26B).

The sensor has 3 pins, and each pin is soldered to a 26 gauge, solid electrical wire. The electrical wires are all covered with 0.045 inch inner diameter miniature heat shrink tubing to avoid shorting the sensor. A 5 Volt battery is used to power the sensor. An Arduino Uno is used to provide meaningful output to the user on when the magnet of the retrieval system is connected with the magnet of the gastric resident system, so the LCD can display "The magnets are connected."

Example 13

Figure 27A:
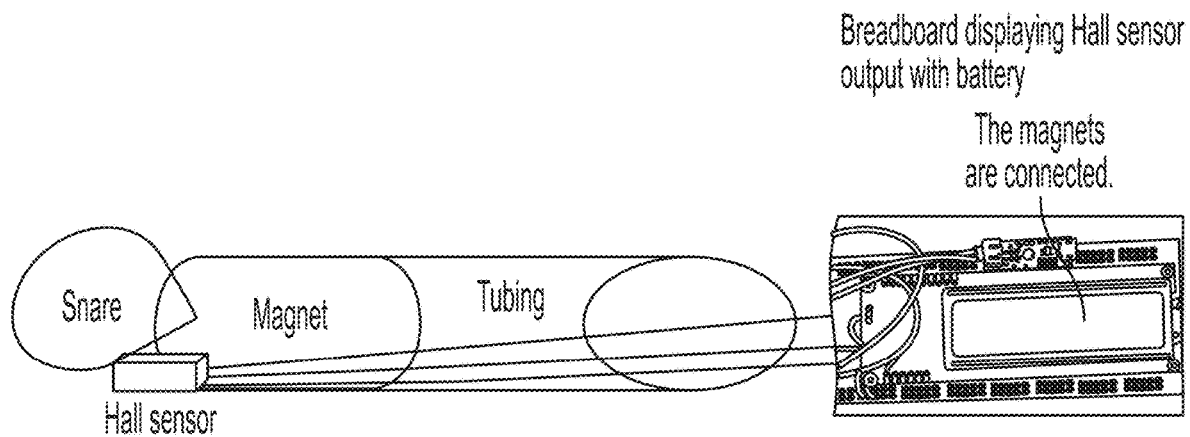
FIG. 27A is a schematic illustration of an exemplary system, according to one set of embodiments.
Figure 27B:
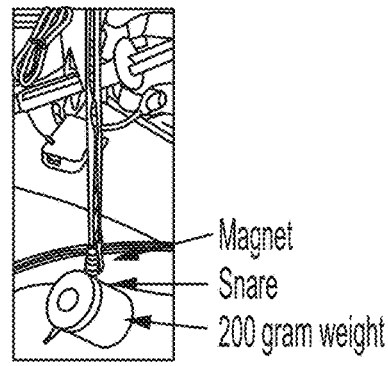
FIG. 27B is a photograph of an exemplary system, according to one set of embodiments.

In another implementation shown in FIG. 27A, the retrieval system incorporates a single-oval polypectomy snare in addition to a series of ring neodymium magnets with ¼ inch outer diameter and ¹⁄₁₆ inch inner diameter and Allegro A1324 linear hall effect sensor all housed in Tygon tubing with outer diameter ¼ inch and inner diameter of ³⁄₁₆ inch. The snare is only activated to expand once the retrieval system is in contact with the magnet of the gastric resident system. The snare can hold a weigh of at least 200 grams as shown in FIG. 27B.

The sensor has 3 pins, and each pin is soldered to a 26 gauge, solid electrical wire. The electrical wires are all covered with 0.045 inch inner diameter miniature heat shrink tubing to avoid shorting the sensor. A 5 Volt battery is used to power the sensor. An Arduino Uno is used to provide meaningful output to the user on when the magnet of the retrieval system is connected with the magnet of the gastric resident system, so the LCD can display "The magnets are connected."

Exemplary Embodiments

1. An article with the capacity for sustained drug delivery in a mammal capable of transesophageal administration and transesophageal retrieval composing of a series of drug delivery systems attached to a superelastic retention frame
   a. Wherein the article components are made of biocompatible materials
   b. Wherein the drug delivery article can safely reside in the stomach with a gastric retentive component
   c. Wherein the article is capable of minimizing burst release of drug
2. The article according to embodiment 1 wherein the article has the capacity to retain its final shape while stored for 1-365 days.
3. The article according to embodiment 1 where the article is composed of a retention frame which is composed of but not limited to:
   a. Low modulus elastomer wire such as silicone or polyurethane
   b. Elastic wire such as a superelastic alloy or other shape memory material like nitinol
   c. Hollow heat-shaped elastomer tubing
   d. Hollow shape-memory alloy
4. The article according to embodiment 1 where the drug delivery system is made of series of cylindrical pills made of drug mixed with a nonerodable matrix such as vinylpolysiloxane, polydimethylsiloxane, polycaprolactone, polyethylene, or polyethylene-vinyl acetate, and each pill has a 0.5 mm hole inside it.
5. The article according to embodiment 1 and embodiment 4 where the drug is doxycycline hyclate, moxifloxacin, pyrazinamide, isoniazid, or moxifloxacin.
6. The article according to embodiment 1 and 4 where the diameter of the cylindrical pills is 4 mm and the height is more than 5 mm.
7. The article according to embodiment 1 and 4 where the diameter of the cylindrical pills is 4 mm and the height is more than 5 mm.
8. The article according to embodiment 1 and 4 where the pills are coated with Eudragit RS PO, Eudragit NM 30D, polycaprolactone, ethylcellulose, cellulose acetate, cellulose acetate butyrate, polydimethysiloxane, or vinylpolysiloxane.
9. The article according to embodiment 1 and 4 where the pills have 2 or more drug powders in them.
10. The article according to embodiment 1 and 4 where the pills contain excipients such as polyethylene glycol to tune the release rate of the drug.
11. The article according to embodiment 1 where the drug delivery system is made of series of cylindrical pills made of concentric cylinders with each a different concentration of drug in each cylinder and made of drug mixed with vinylpolysiloxane, polydimethylsiloxane, polycaprolactone, polyethylene, or polyethylene-vinyl acetate, and each pill has a 0.5 mm hole inside it.
12. The article according to embodiment 1 and embodiment 11 where the drug is doxycycline hyclate, moxifloxacin, pyrazinamide, isoniazid, or moxifloxacin.
13. The article according to embodiment 1 and 11 where the diameter of the cylindrical pills is 4 mm and the height is more than 5 mm.
14. The article according to embodiment 1 and 11 where the diameter of the cylindrical pills is 4 mm and the height is more than 5 mm.
15. The article according to embodiment 1 and 11 where the pills are coated with Eudragit RS PO, Eudragit NM 30D, polycaprolactone, ethylcellulose, cellulose acetate, cellulose acetate butyrate, polydimethysiloxane, or vinylpolysiloxane.
16. The article according to embodiment 1 and 11 where the pills have 2 or more drug powders in them.
17. The article according to embodiment 1 and 11 where the pills contain excipients such as polyethylene glycol to tune the release rate of the drug.
18. The article according to embodiment 1 where the drug delivery system is made of series of cylindrical pills made of hollow flexible tubing enclosing the drug powder, retention frame, and has micro-drilled holes in the tubing to facilitate drug release
19. The article according to embodiment 1 and embodiment 18 where the drug is doxycycline hyclate, moxifloxacin, pyrazinamide, isoniazid, or moxifloxacin.
20. The article according to embodiment 1 and embodiment 18 where the micro-drilled hole have porous thin polymer films to control the rate of drug release.
21. The article according to embodiment 1 where the retention frame and pills are enclosed in flexible tubing that may be permeable to fluid or impermeable to fluid and have holes to allow access to fluid.
22. The article according to embodiment 1 where the retention frame is immersed in silicone adhesive at both ends.
23. The article according to embodiment 1 where the article has a magnetic bead on one or both ends to facilitate retrieval via nasogastric or endoscopic tube.
24. The article according to embodiment 1 where the article shape can be fitted inside a nasogastric or endoscopic tube as well as standard larger feeding tubes for veterinary use.

25. An article with the capacity for drug delivery in a mammal having gastric retention for greater than 1 month:
   a. Wherein the article is compatible with transesophageal administration through a nasogastric or endoscopic tube.
   b. Wherein the article is of dimensions compatible with gastric retention.
   c. Wherein the article is at least 28.66 cm long to hold at least 10 grams of API.
   d. Wherein the article is compatible with transesophageal retrieval through a nasogastric or endoscopic tube.
26. The article according to embodiment 25 wherein the article has the capacity to retain its final shape while stored for 1-365 days.
27. The article according to embodiment 25 wherein the article shape can be stretched into a straight configuration while being administered and then revert to an altered shape of a J-hook with a minimum diameter of 2 cm when it reaches the stomach.
28. The article according to embodiment 25 wherein the article shape can be stretched into a straight configuration while being administered and then revert to an altered shape of a sphere with a minimum diameter of 2 cm when it reaches the stomach.
29. The article according to embodiment 25 wherein the article shape can be stretched into a straight configuration while being administered and then revert to an altered shape of a series of circles like a cylinder with a minimum diameter of the circle being 2 cm when it reaches the stomach.
30. The article according to embodiment 25 wherein the article shape can be stretched into a straight configuration while being administered and then revert to an altered shape of a toroid with a minimum diameter of 2 cm of the circular sections when it reaches the stomach.
31. The article according to embodiment 25 where the maximum force to administer the article through a nasogastric or endoscopic tube is 20 N.
32. The article according to embodiment 25 where the article is composed of a retention frame which is composed of but not limited to:
   a. Low modulus elastomer wire such as silicone or polyurethane
   b. Elastic wire such as a superlastic alloy or other shape memory material
   c. Hollow heat-shaped elastomer tubing
   d. Hollow shape-memory alloy
33. The article according to embodiment 25 and 32 where the retention frame is encapsulated inside an elastomeric hollow tubing, which has a cross-section of a circle, cube, triangle, and other polygons.
34. The article according to embodiment 25 and 32 where the retention frame is encapsulated inside an elastomeric multi-lumen tubing.
35. The article according to embodiment 25 and 32 where the article is made of a multi-material complex blend of a retention wire and elastomeric tubing.
36. The article according to embodiment 25 and 32 where the retention frame is on the outside of the elastomeric tubing.
37. The article according to embodiment 25 and 32 where the retention frame is immersed in silicone adhesive and besides a magnetic bead.
38. The article according to embodiment 25 where the article has a magnetic bead on one or both ends to facilitate retrieval via nasogastric or endoscopic tube.
39. The article according to embodiment 25 where the maximum force to retrieve the article through a nasogastric or endoscopic tube is 20 N.
40. The article according to embodiment 25 where the article shape can be fitted inside a nasogastric or endoscopic tube as well as standard larger feeding tubes for veterinary use.
41. A magnetic retrieval system for use in a large mammal:
   a. Wherein the system is compatible with transesophageal passage through a nasogastric or endoscopic tube.
   b. Wherein the system has dimensions compatible with access to the stomach
   c. Wherein the system has a sensor element to detect the distance from a magnet on the gastric resident system
   d. Wherein the system has a magnet to attach to the gastric resident system
   e. Wherein the system has an output signal for the user to indicate contact of the retrieval system with the gastric resident system
   f. Wherein the system can hold the weight and retrieve the gastric resident system
42. The system according to embodiment 41 wherein the system uses flexible tubing with outer diameter less than ¼ inch to house the sensor and magnet.
43. The system according to any one of embodiments 41-42 wherein the system uses a Hall effect sensor.
44. The system according to any one of embodiments 41-43 wherein the system uses cylindrical or ring magnets with maximum outer diameter of 3/16 inches.
45. The system according to any one of embodiments 41-44 wherein the system uses barbs.
46. The system according to any one of embodiments 41-45 wherein the system uses a LCD display, LED lights, or sound to indicate the distance of the retrieval system from the gastric resident system.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. An article for transesophageal administration to a subject, comprising:
    a plurality of discrete polymer matrices each comprising a polymeric material,
    each of the plurality of discrete polymer matrices having a hollow core;
    a therapeutic agent associated with each of the plurality of discrete polymer matrices; and
    a removable elastic wire disposed within the hollow cores thereby linking the plurality of discrete polymer matrices,
    wherein the plurality of discrete polymer matrices are encapsulated by a removable elastomeric overtube, wherein the article is configured to obtain a first, straightened configuration sized and adapted for transesophageal administration and/or retrieval to the subject when disposed within the removable elastomeric overtube, wherein, the article is configured to obtain a second, coiled configuration sized and adapted for gastric retention thereby preventing passage through the pylorus of the subject upon removal of the plurality of discrete polymer matrices from the removable elastomeric overtube, wherein change between the straightened configuration and the coiled configuration is mediated by the removable elastic wire, wherein the article undergoes elastic deformation when the plurality of discrete polymer matrices are removed from the removable elastomeric overtube, wherein the article has an uncoiled length of greater than or equal to 28 cm when in the first configuration, and wherein the therapeutic agent is present in the article in an amount greater than or equal to 3 grams.

2. An article as in claim 1, wherein the article is sized and adapted for retention within a gastric cavity of a subject for greater than or equal to 1 day.

3. An article as in claim 1, wherein the shape of the polymeric material is configured to be reconfigured such that the article has a maximum overall diameter of greater than or equal to 2 cm in the second configuration.

4. An article as in claim 1, wherein the article has an administration force of less than or equal to 20 N.

5. An article as in claim 1, wherein the article further comprises a magnetic component.

6. An article as in claim 1, wherein the elastic wire comprises a superelastic alloy and/or shape memory material.

7. An article as in claim 1, wherein the polymeric material comprises vinylpolysiloxane, polydimethylsiloxane, polycaprolactone, polyethylene, polyethylene-vinyl acetate, or combinations thereof.

8. An article as in claim 1, wherein the therapeutic agent is selected from the group consisting of doxycycline hyclate, moxifloxacin, pyrazinamide, ethambutol, isoniazid, rifampicin, Streptomycin, interferon, peginterferon, ribavirin, paritaprevir, simepravir, grazoprevir, ladispavir, ombitasvir, elbasavir, daclatasvir, and sofosbuvir.

9. An article as in claim 1, wherein the article has an overall diameter of greater than or equal to 1 mm and less than or equal to 20 mm when in the first configuration.

10. An article as in claim 1, wherein each polymeric material is further encapsulated by a pH-sensitive polymeric coating.

11. An article as in claim 1, wherein the polymeric material comprises a plurality of micro-drilled holes.

* * * * *